US011708556B2

(12) United States Patent
Gale et al.

(10) Patent No.: US 11,708,556 B2
(45) Date of Patent: Jul. 25, 2023

(54) TISSUE SAMPLE PROCESSING SYSTEM AND ASSOCIATED METHODS

(71) Applicant: University of Utah Research Foundation, Salt Lake City, UT (US)

(72) Inventors: Bruce K. Gale, Salt Lake City, UT (US); Douglas T. Carrell, Salt Lake City, UT (US); Kristin Murphy, Salt Lake City, UT (US); Jim Hotaling, Salt Lake City, UT (US); Jiyoung Son, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1172 days.

(21) Appl. No.: 15/520,795

(22) PCT Filed: Oct. 20, 2015

(86) PCT No.: PCT/US2015/056494
§ 371 (c)(1),
(2) Date: Apr. 20, 2017

(87) PCT Pub. No.: WO2016/064896
PCT Pub. Date: Apr. 28, 2016

(65) Prior Publication Data
US 2017/0306288 A1 Oct. 26, 2017

Related U.S. Application Data

(60) Provisional application No. 62/066,232, filed on Oct. 20, 2014.

(51) Int. Cl.
*C12M 1/00* (2006.01)
*A61B 17/435* (2006.01)
(Continued)

(52) U.S. Cl.
CPC ........... *C12M 47/04* (2013.01); *A61B 17/435* (2013.01); *A61D 19/00* (2013.01);
(Continued)

(58) Field of Classification Search
None
See application file for complete search history.

(56) References Cited

U.S. PATENT DOCUMENTS 5,514,537 A 5/1996 Chandler
7,704,728 B2 4/2010 Takayama et al.
(Continued)

FOREIGN PATENT DOCUMENTS

JP 2005/518794 A 6/2005
JP 2012/073268 A 4/2012
(Continued)

OTHER PUBLICATIONS

Nivedita, Nivedita; Papautsky, Ian; "Continuous separation of blood cells in spiral microfluidic devices" Biomicrofluidics, 7, 054101, 2013 (Year: 2013).*
(Continued)

*Primary Examiner* — David W Berke-Schlessel
(74) *Attorney, Agent, or Firm* — Thorpe North & Western LLP

(57) ABSTRACT

A tissue sample processing system and associated methods is disclosed and described. The tissue sample processing system (100) can include a microfluidic separating system (110). The microfluidic separating system (110) can include a fluid channel to receive a carrier fluid (104) and a tissue sample (102), and a plurality of outlets. Flow of the carrier fluid (104) and the tissue sample (102) in the fluid channel can facilitate segregation of materials in the tissue sample (102) based on size into a plurality of size fractions, such that each one of the plurality of outlets receives a different
(Continued)

size fraction of the materials in the tissue sample. In addition, the sample processing system (100) can comprise a cryopreservation system (120) associated with at least one of the plurality of outlets to freeze the material in the tissue sample (102) associated with the at least one of the plurality of outlets.

17 Claims, 20 Drawing Sheets

(51) Int. Cl.
| | | |
|---|---|---|
| *C12M 3/06* | (2006.01) | |
| *C12N 5/071* | (2010.01) | |
| *A61D 19/00* | (2006.01) | |
| *B01L 3/00* | (2006.01) | |
| *G01N 30/00* | (2006.01) | |

(52) U.S. Cl.
CPC ....... *B01L 3/502761* (2013.01); *C12M 23/16* (2013.01); *C12N 5/0612* (2013.01); *G01N 30/0005* (2013.01); *B01L 3/502738* (2013.01); *B01L 2200/0652* (2013.01); *B01L 2300/0816* (2013.01); *B01L 2300/0864* (2013.01); *G01N 2030/002* (2013.01)

(56) References Cited

U.S. PATENT DOCUMENTS

| | | | |
|---|---|---|---|
| 7,855,078 | B2 | 12/2010 | Evans |
| 8,080,422 | B2 | 12/2011 | Neas et al. |
| 8,186,913 | B2 | 5/2012 | Toner et al. |
| 8,208,138 | B2 | 6/2012 | Papautsky et al. |
| 8,263,023 | B2 | 9/2012 | Le Vot et al. |
| 8,535,536 | B1 | 9/2013 | Gale et al. |
| 8,679,751 | B2 | 3/2014 | Huang |
| 8,778,279 | B2 | 7/2014 | Durack |
| 8,784,012 | B2 | 7/2014 | Toner et al. |
| 8,807,879 | B2 | 8/2014 | Toner et al. |
| 9,523,075 | B2 * | 12/2016 | Takayama ......... B01L 3/502753 |
| 2006/0229367 | A1 | 10/2006 | Neas et al. |
| 2008/0187991 | A1 | 8/2008 | Takayama et al. |
| 2009/0014360 | A1 | 1/2009 | Toner et al. |
| 2009/0188795 | A1 | 7/2009 | Oakey et al. |
| 2010/0234674 | A1 * | 9/2010 | Wheeler ............. F16K 99/0001 600/35 |
| 2011/0076712 | A1 | 3/2011 | Gilligan et al. |
| 2011/0096327 | A1 | 4/2011 | Papautsky et al. |
| 2012/0292233 | A1 | 11/2012 | Toner et al. |
| 2013/0011210 | A1 | 1/2013 | Toner et al. |
| 2013/0130226 | A1 | 5/2013 | Lim et al. |
| 2014/0199720 | A1 | 7/2014 | Qiu et al. |
| 2014/0248621 | A1 | 9/2014 | Collins |
| 2014/0273179 | A1 | 9/2014 | Sharpe et al. |
| 2014/0326339 | A1 | 11/2014 | Toner et al. |
| 2014/0374324 | A1 | 12/2014 | Papautsky et al. |

FOREIGN PATENT DOCUMENTS

| | | |
|---|---|---|
| JP | 2013/521001 A | 6/2013 |
| WO | WO 03/072765 A1 | 9/2003 |
| WO | WO2004/108011 A1 | 12/2004 |
| WO | WO 2005/023391 A2 | 3/2005 |
| WO | WO 2011109762 A1 | 9/2011 |
| WO | WO2013/040428 A1 | 3/2013 |
| WO | WO2013/115725 A1 | 8/2013 |
| WO | WO 2013129947 A1 | 9/2013 |
| WO | WO2014/085801 A1 | 6/2014 |

OTHER PUBLICATIONS

Extended European Search Report dated Jul. 12, 2018, in EP Application No. 15852164.1, filed Oct. 20, 2015; 8 pages.

Bhagat et al.; "Microfluidics for Cell Separation." Med Biol Eng Comput; Springer; Oct. 2010; vol. 48, Issue 10; pp. 999-1014.

Davis et al.; "Deterministic Hydrodynamics: Taking Blood Apart." PNAS; Oct. 3, 2006; vol. 103, Issue 40; pp. 14779-14784.

Kuntaegowdanahalli et al.; "Inertial Microfluidics for Continuous Particle Separation in Spiral Microchannels." Lab on a Chip; The Royal Society of Chemistry; Jul. 21, 2009; vol. 9, Issue 20; pp. 2973-2980.

Li et al.; "On-Chip Cryopreservation of Living Cells." Journal of the Association for Laboratory Automation; SAGE; Apr. 2010; pp. 99-106.

Nivedita et al.; "Continuous Separation of Blood Cells in Spiral Microfluidic Devices." Biomicrofluidics; AIP Publishing; Sep. 2013; vol. 7, Issue 5; pp. 054101-1-054101-14.

PCT Application No. PCT/US15/56494; Filing date Oct. 20, 2015; Kristin Murphy, International Search Report dated Feb. 10, 2016, 12 Pages.

Schuster et al.; "Isolation of Motile Spermatozoa from Semen Samples Using Microfluidics." Reproductive BioMedicine Online; Elsevier; 2003; vol. 7, Issue 1; pp. 75-81.

Wu et al.; "Separation of Leukocytes from Blood Using Spiral Channel with Trapezoid Cross-Section." Analytical Chemistry; ACS Publications; Oct. 1, 2012; vol. 84, Issue 21; pp. 9324-9331.

\* cited by examiner

TISSUE SAMPLE PROCESSING SYSTEM AND ASSOCIATED METHODS

RELATED APPLICATION

This application claims the benefit of U.S. Provisional Application No. 62/066,232, filed Oct. 20, 2014, which is incorporated herein by reference.

BACKGROUND

Approximately one in eight couples in the western world is not able to conceive spontaneously after a one-year period of unprotected intercourse. In nearly half of those cases, the male partner has one or more semen parameters that are below the World Health Organization (WHO) cut-offs for normozoospermia. Non-obstructive azoospermia (NOA), the most severe form of male factor infertility in which men have no sperm in their ejaculate, impacts 10% of these cases. Conception for NOA patients is dependent on a surgical procedure to extract sperm directly from the testis, called microsurgical testicular sperm extraction (mTESE). mTESE involves a surgical procedure where seminiferous tubules of the testis are removed under an operating microscope, followed by manual microscopic tissue examination by an embryologist in order to identify foci of spermatogenesis within the parenchymal tissue. If sperm are identified, tissue specimens are cryopreserved in bulk and the couple will undergo in vitro fertilization (IVF) in an attempt to become pregnant.

mTESE procedures are often unsuccessful due to major limitations with current techniques. For example, because IVF is a time-sensitive procedure that requires coordination of oocyte collection and sperm preparation, it is important that sperm isolated from mTESE procedures be cryopreserved for use at a later date. When spermatocytes are identified within freshly biopsied tissue, current cryopreservation techniques entail bulk tissue storage within relatively large storage tubes. As a consequence, it is difficult to relocate the spermatocyte(s) once tissue is thawed. For example, mTESE procedures currently rely on manual microscopic inspection of testicular tissue specimens to identify sperm, a long and labor-intensive process. After sperm-containing samples are cryopreserved and then thawed, sperm must be re-located and separated from other cell types before they can be used for ART (assistive reproductive technologies) therapies. This process is highly inefficient and often sperm are missed or lost. Thus, sperm are frequently not found by embryologists after searching microscopic fields of testicular tissue for up to 12 hours. If sperm are initially identified and tissue is cryopreserved for IVF, in many cases the sperm is not recovered again after the tissue is thawed. In addition, this method allows for only one opportunity to thaw sperm for therapeutic use, since multiple freeze/thaw events are detrimental to sperm viability. For these reasons, many NOA patients undergo mTESE procedures only to find that few or no sperm were recovered. These men are left with no alternatives for fathering offspring, and they frequently resort to using donor sperm instead of their own.

The few examples of microfluidic devices that have been developed for sperm isolation utilize the property of sperm motility to separate motile sperm from non-motile sperm. However, because testicular sperm are not motile, existing technologies are not suitable for isolating sperm from NOA testicular tissue specimens.

SUMMARY

A tissue sample processing system and associated methods is disclosed and described. In one aspect, the tissue sample processing system can comprise a microfluidic separating system. The microfluidic separating system can include a fluid channel to receive a tissue sample, and a plurality of outlets. Flow of the tissue sample in the fluid channel can facilitate segregation of materials in the tissue sample based on size into a plurality of size fractions, such that each one of the plurality of outlets receives a different size fraction of the materials in the tissue sample. In addition, the sample processing system can comprise a cryopreservation system associated with at least one of the plurality of outlets to freeze the material in the tissue sample associated with the at least one of the plurality of outlets.

In one aspect, a tissue sample processing system is disclosed that can include a microfluidic separating system having a fluid channel to receive a carrier fluid and a tissue sample, and a plurality of outlets. Flow of the carrier fluid and the tissue sample in the fluid channel can facilitate segregation of materials in the tissue sample based on size into a plurality of size fractions, such that each one of the plurality of outlets receives a different size fraction of the materials in the tissue sample. In addition, the tissue sample processing system can include a sorting system associated with at least one of the plurality of outlets to sort a plurality of aliquots of the material in the tissue sample associated with the at least one of the plurality of outlets.

In another aspect, a tissue sample processing system is disclosed that can include a microfluidic separating system having a fluid channel to receive a carrier fluid and a tissue sample, and a plurality of outlets. Flow of the carrier fluid and the tissue sample in the fluid channel can facilitate segregation of materials in the tissue sample based on size into a plurality of size fractions, such that each one of the plurality of outlets receives a different size fraction of the materials in the tissue sample. In addition, the tissue sample processing system can include a concentrating system associated with at least one of the plurality of outlets to concentrate a size fraction of the material in the tissue sample associated with the at least one of the plurality of outlets.

In one aspect, a method of separating sperm cells is disclosed. The method can comprise obtaining a microfluidic separating system having a fluid channel and a plurality of outlets. The method can also comprise disposing a carrier fluid in the fluid channel. In addition, the method can comprise disposing a sperm sample in the fluid channel. Sperm are uniquely shaped and often not amenable to separations using traditional methods, especially when they are non-motile. Flow of the carrier fluid and the sperm sample in the fluid channel can facilitate segregation of materials in the sperm sample based on size into a plurality of size fractions, such that each one of the plurality of outlets receives a different size fraction of the materials in the sperm sample, including non-motile sperm.

In another aspect, a method of separating non-motile sperm cells from a tissue sample is disclosed. The method can comprise flowing a sperm sample through a fluid channel under laminar flow conditions, wherein a cross-flow in the fluid channel facilitates segregation of non-motile sperm cells within an inner fluid flow layer. The method can also comprise spatially separating the inner fluid flow layer.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
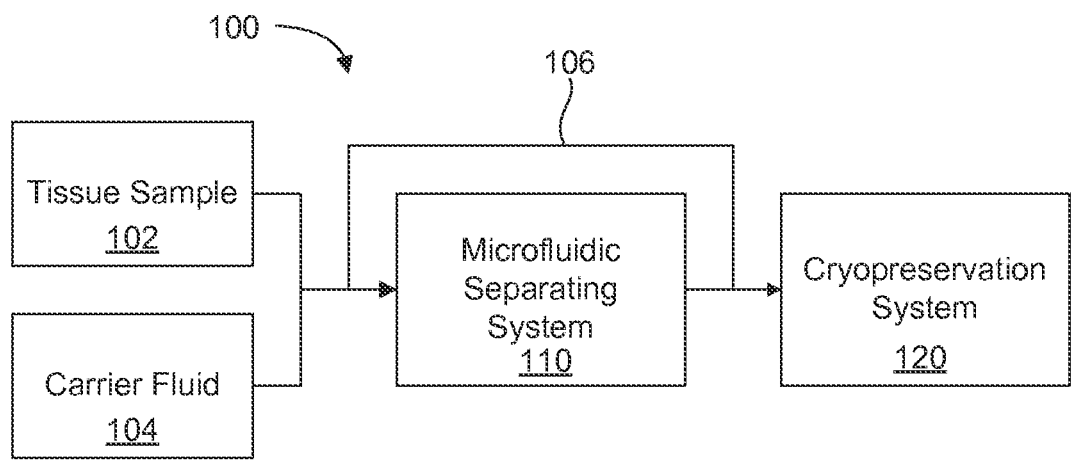
FIG. 1 is a schematic illustration of a tissue sample processing system in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a sample" includes reference to one or more of such materials and reference to "injecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in, the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Tissue Sample Processing

FIG. 1 schematically illustrates a tissue sample processing system 100 in accordance with an example of the present disclosure. The tissue sample processing system 100 can include a microfluidic separating system 110 to receive a tissue sample 102 and a carrier fluid 104, if desired. As described in more detail below, flow of the tissue sample 102 and the carrier fluid 104 in the microfluidic separating system 110 facilitates segregation of materials in the tissue sample based on size into a plurality of size fractions. Thus, the microfluidic separating system 110 can be configured to separate a cell of a specific type (based on size) from other cells in the tissue sample. In one example, the tissue sample 102 can comprise a sperm or semen sample, thus including sperm cells (e.g., motile and/or non-motile sperm cells). In some cases, the tissue sample or sample fluid can be a fluid sperm sample without an added separate carrier fluid (i.e. carrier fluid is native seminal fluid). Alternatively, an additional carrier fluid can be added to facilitate desired fluid flow. The microfluidic separating system 110 can be configured to separate sperm cells from other cells in the tissue sample, such as separating non-motile sperm cells from red blood cells (RBC). In one aspect, the microfluidic separating system 110 can sort several cell types, such as spermatagonial stem cells or other sperm precursors, which can potentially be used to generate sperm. The tissue sample processing system 100 can be used for the enrichment of sperm cells over somatic tissue cells. Output of the microfluidic separating system 110 can be reprocessed 106 to improve the resolution of a desired cell type in the output. Any suitable type of microfluidic separating system 110 can be utilized, such as those described below.

The tissue sample processing system 100 can also include a cryopreservation system 120 to freeze the material in the tissue sample 102 that is desired output from the microfluidic separating system 110. The cryopreservation system 120 can include any suitable type of cryogenic freezer, such as a liquid nitrogen freezer or a mechanical freezer.

Figure 2:
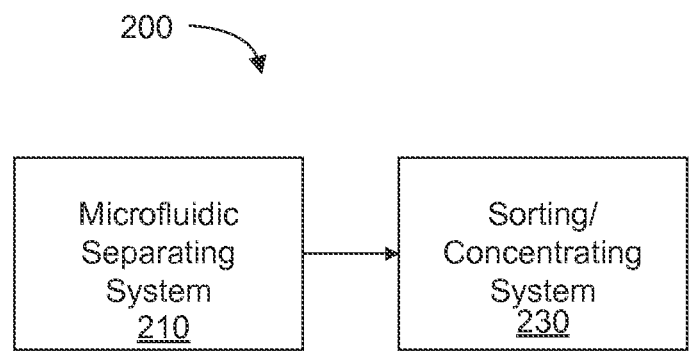
FIG. 2 is a schematic illustration of a tissue sample processing system in accordance with another example of the present disclosure.

FIG. 2 schematically illustrates a tissue sample processing system 200 in accordance with another example of the present disclosure. The tissue sample processing system 200 can include a microfluidic separating system 210, as described above. In this case, the tissue sample processing system 200 includes a sorting and/or concentrating system 230 to sort a plurality of aliquots of the material in the tissue sample. Any suitable sorting and/or concentrating system can be utilized, such as those described below. In general, a sorting system sorts material in the tissue sample (e.g., particles or cells) into aliquots, which may comprise a given quantity (e.g., a numerical range) of a desired cell type. A concentrating system improves the resolution of a particular cell type to remove unwanted cells from a population, such as by concentrating a size fraction of material in a tissue sample. Although the sorting and/or concentrating system 130 is represented by a single block in the diagram of FIG. 2, it should be understood that a sorting system and a concentrating system can be independent of one another. Thus, the tissue sample processing system 200 can include either a sorting system or a concentrating system, or both. In one aspect, a single system can perform both sorting and concentrating functions. When the tissue sample processing system 200 can includes separate sorting and concentrating system, the output flow can be in any order. For example, a sorting system can deliver output to a concentrating system or a concentrating system can deliver output to a sorting system.

Figure 3:
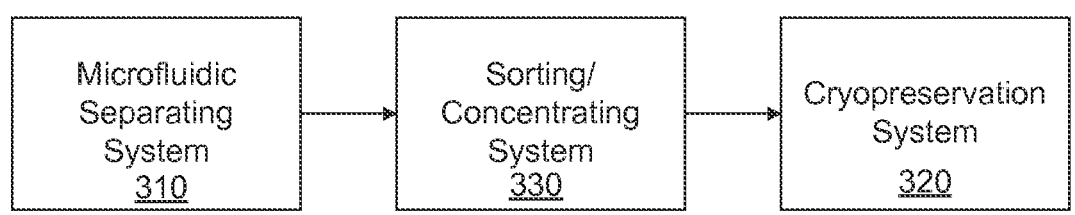
FIG. 3 is a schematic illustration of a tissue sample processing system in accordance with yet another example of the present disclosure.

FIG. 3 schematically illustrates a tissue sample processing system 300 in accordance with yet another example of the present disclosure. The tissue sample processing system 300 can include a microfluidic separating system 310 and a sorting and/or concentrating system 330, as described above. In this case, the tissue sample processing system 300 also includes a cryopreservation system 320, as described above. Thus, output from the sorting and/or concentrating system 330 can be delivered to the cryopreservation system 320 for freezing and preservation. For example, concentrated and/or sorted material from the sorting and/or concentrating system 330 can be delivered to the cryopreservation system 320 and frozen.

Figure 4:
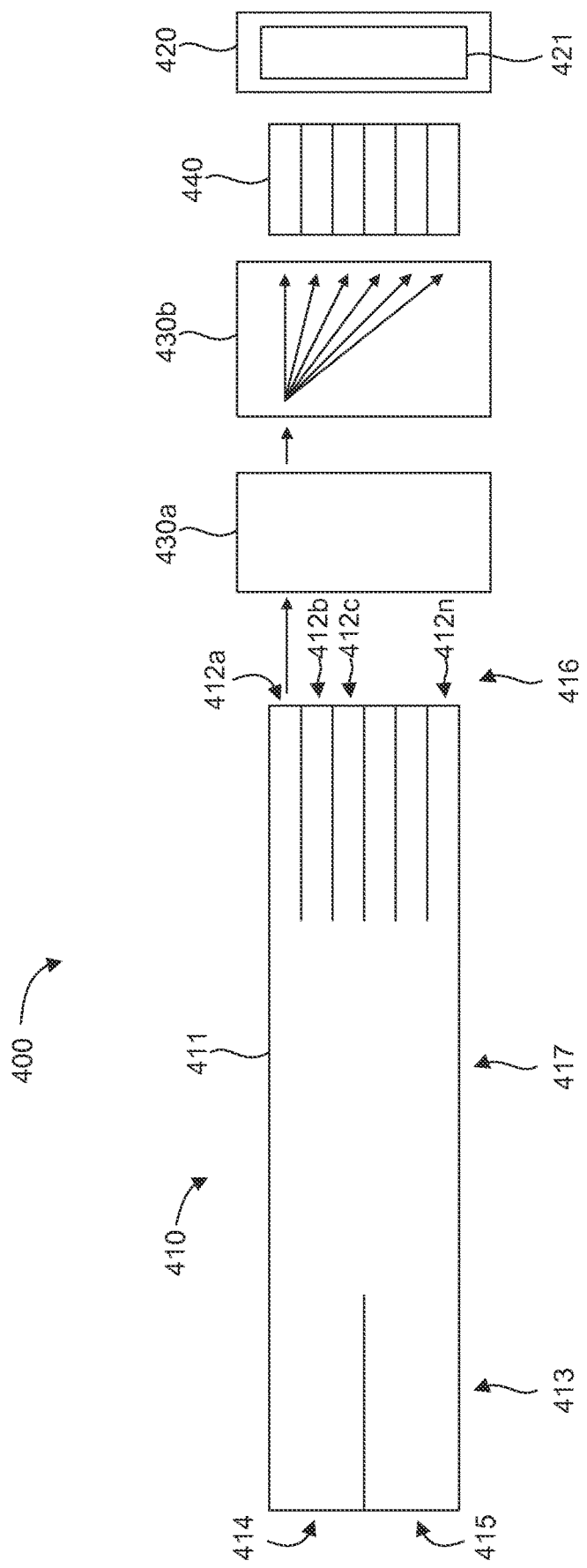
FIG. 4 is a schematic illustration of a tissue sample processing system in accordance with a further example of the present disclosure.

FIG. 4 illustrates a tissue sample processing system 400 in accordance with yet another example of the present disclosure. The tissue sample processing system 400 can include a microfluidic separating system 410, a concentrating system 430a, a sorting system 430b, and a cryopreservation system 420. FIG. 4 shows several specific aspects of a tissue sample processing system in accordance with the present disclosure. For example, the microfluidic separating system 410 can include a fluid channel 411 to receive a carrier fluid and a tissue sample, and a plurality of outlets 112a-n. Flow of the carrier fluid and the tissue sample in the fluid channel 411 can facilitate segregation of materials in the tissue sample based on size into a plurality of size fractions, such that each one of the plurality of outlets 412a-n receives a different size fraction of the materials in the tissue sample. Although the fluid channel 411 is illustrated as having a "straight" configuration, it should be recognized that the fluid channel can have any suitable configuration, such as a spiral configuration, as discussed below.

In one aspect, the fluid channel 411 can include an inlet zone 413 having a carrier fluid inlet 414 to receive a carrier fluid and a tissue sample inlet 415 to receive a tissue sample. The fluid channel 411 can also include an outlet zone 416 having the plurality of outlets 412a-n. In addition, the fluid channel 411 can include a transport region 417 between the inlet zone 413 and the outlet zone 416. The transport region 417 can be open to the carrier fluid and the tissue sample. A cross-flow in the transport region 417 can facilitate segregation of materials in the tissue sample based on size into a plurality of size fractions, and each one of the plurality of outlets 412a-n can receive a different size fraction of the materials in the tissue sample. For example, the outlets 412a-n can be spatially separated to retrieve various size fractions based on design parameters. Although six outlets are illustrated, any suitable number of outlets may be included. As used herein, the term "cross-flow" is used to describe flow and/or forces acting transversely on particles in the fluid channel 411, which may cause segregation of materials into different size fractions. Thus, for example, cross-flow in the fluid channel 411 can be due to fluid injected into the fluid channel (e.g., in a straight channel configuration) and/or due to flow along a spiral channel, which generates a lateral, secondary vortex flow (e.g., flow that generates a Dean drag force), discussed in more detail below. In one aspect, the spiral configuration can be a substantially planar spiral. Alternatively, or in addition, cross-flow in the fluid channel 411 can be induced via dedicated flow inlets along the channel which allow introduction of a cross-flow fluid.

The concentrating system 430a can be associated with one or more of the outlets 412a-n to concentrate a size fraction of the material in the tissue sample associated with the outlets 412a-n. As shown in FIG. 4, the cryopreservation unit is associated with outlet 411a. The concentrating system 430a can include one or more outlets (not specifically illustrated) to provide output material to the sorting system 430b, which can be associated with the one or more outlets of the concentrating system 430a. Thus, once a given size fraction of material has been concentrated, the material can be output to the sorting system 430b to sort a plurality of aliquots of the material in the tissue sample delivered from the concentrating system 430a. In one aspect, the sorting system 430b can be used to sort from about 1 to about 20 non-motile sperm cells into each aliquot. In a more particular aspect, the sorting system 430b can be used to sort from about 1 to about 10 non-motile sperm cells into each aliquot. In an even more particular aspect, the sorting system 430b can be used to sort a single non-motile sperm cell into each aliquot. In one aspect, the tissue sample processing system 400 may not include a concentrating system. Therefore the sorting system 430b can be associated with one or more of the outlets 412a-n of the microfluidic separating system 410. The aliquots of tissue sample material can be delivered to, and stored in, any suitable container or chamber 440 for cryopreservation, such as a cryotube or a cryostraw. Although various dimensions can be used, typical sperm cell aliquots can be from 10 to about 2000 microliters, in some cases from 50 to 500 microliters, and in other cases less than about 200 microliters.

The cryopreservation unit 420 can be configured to receive material from the sorting system 430b, such as by receiving the containers 440 with the aliquots of tissue sample material. The cryopreservation unit 420 can include a cryogenic freezer 421 to freeze the aliquots of tissue sample material. In one aspect, the tissue sample processing system 400 may not include a concentrating system or a sorting system. Therefore the cryopreservation unit 420 can be associated with one or more of the outlets 412a-n of the microfluidic separating system 410.

In one aspect, the tissue sample processing system 400 can divide an input volume of sperm samples into predetermined aliquots and deliver them to cryopreservation chambers built on the "sorting chip" to divide up collected sperm populations in a relatively uniform manner. The fluid can therefore be directed to the sorting system 430b in which multiple aliquots of sperm-containing fluid can be individually stored and then independently frozen and thawed. The tissue sample processing system 400 can therefore receive testicular tissue specimens as input and output sorted and cryopreserved sperm without impairing sperm cell viability. In one aspect, storage chambers may be compatible with micromanipulators used in human in vitro fertilization laboratories in order to dispense sperm.

Time-sensitivity of sperm cells makes such an approach desirable so that cells can be thawed at different times should initial IVF procedures fail. Multiple aliquot storage channels can be arranged in series to provide any number of discrete compartments which can be independently frozen and thawed. Thus, the tissue sample processing system 400 can be a micro-scale sperm cryopreservation system capable of dividing isolated sperm into aliquots that can be individually cryopreserved and easily recovered post-thaw for IVF.

In one aspect, the tissue sample processing system 400 can be automated for sorting of individual sperm into groups for multiple cryopreservation aliquots. Thus, the tissue sample processing system 400 can automate the tissue processing steps during mTESE procedures, such as dissociating human testicular tissue pieces into single cells and separate spermatocytes from all other somatic cell types and debris. An automated system can save clinicians time in sample processing, as well as reduce human-associated error, increase efficiency, and increase consistency of results. In another aspect, the tissue sample processing system 400 can comprise a closed microfluidic "system" that provides cell separation, sorting, and cryopreservation. A closed system can promote sterility and prevent contamination while minimizing sample loss. It should be recognized however that the cryopreservation unit and/or the sorting system can be used independent of the sperm isolating fluid channel.

In one aspect, the tissue sample processing system 400 can include components for tissue dissociation into single cells, because human mTESE specimens will typically consist of tissue pieces, not individual cells. Mechanical approaches (e.g., filters, cavitation based devices that rely on high flow rates, and variations on the lateral displacement array that can both shear cell clumps and separate cells simultaneously) can avoid the use of enzymes that may adversely affect cells. In one aspect, antibodies specific to red blood cells can be utilized to aid in removing them from the cell population if red blood cells contaminate the outputs. In one aspect, the tissue sample processing system 400 can have disposable modules for sorting different incoming tissue types (e.g., sperm cells, blood cells, or stem cells). The tissue sample processing system 400 can also include input/output controls, sperm cell counting/imaging components, and software.

The tissue sample processing system 400 has several advantages over current methods used for isolating sperm from testicular sperm extraction biopsy samples from patients with obstructive or nonobstructive azoospermia. For example, automated and microscale flow of testicular tissue will reduce the human error, time, and skill required for manual microscopic separation of sperm cells by human technicians. A microscale sorting and cryopreservation storage system will also allow for multiple aliquots to be thawed individually, in contrast to current techniques, improving IVF outcome. In addition, the tissue sample processing system 400 will increase sperm cell recovery rates compared to current cryopreservation methods. The device can therefore preserve sperm quality (i.e., no cell labeling, enzymes, or lysis is involved).

The tissue sample processing system 400 can comprise any suitable type of sorting structure or configuration. In one example, the fluid channel can utilize split-thin flow principles to separate non-motile sperm cells from other cellular debris in a sample. An example of this technology can be found in U.S. Pat. No. 8,535,536, which is hereby incorporated herein by reference in its entirety. In another example, the fluid channel can comprise a lateral displacement array having posts in a flow for size separation. Small particles can move straight through while larger particles can be deflected to one side.

Figure 5A:
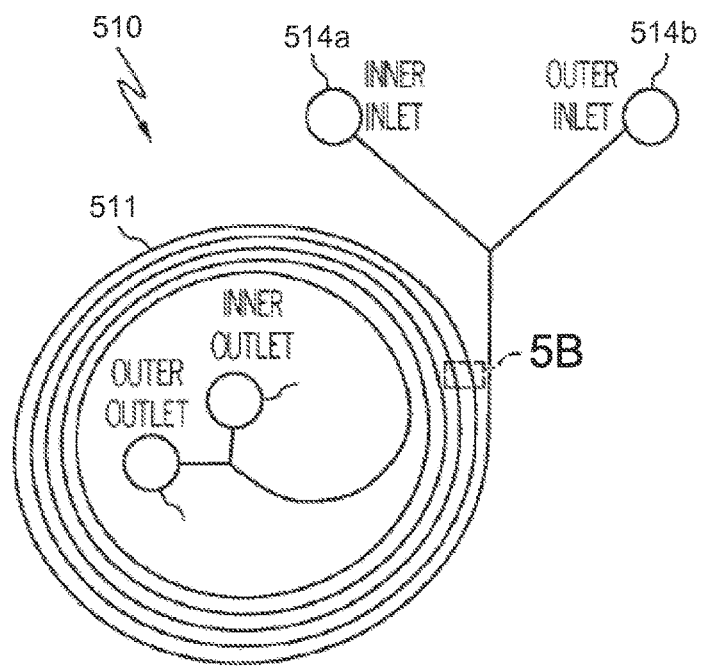
FIG. 5A schematically depicts a spiral microfluidic separating system in accordance with an example of the present disclosure.

FIG. 5A schematically illustrates a microfluidic separating system 510 having a fluid channel 511 with a spiral configuration. The design takes advantage of the inertial lift and viscous drag forces acting on particles of various sizes to achieve differential migration, and hence separation, of microparticles, such as sperm. The dominant inertial forces and the Dean rotation force due to the spiral microchannel geometry cause the larger particles to occupy a single equilibrium position near the inner microchannel wall. The smaller particles migrate to the outer half of the microchannel under the influence of Dean forces resulting in the formation of two distinct particle streams which may be collected in two separate outlets. Due to large lift forces generated by high aspect ratio channels, complete particle separation or filtration can be achieved in short distances even at low flow rates.

The spiral microfluidic separating system 510 comprises an inner inlet 514a, an outer inlet 514b, a fluid channel 511 arranged in a plurality of loops, an inner outlet 512a and an outer outlet 512b.

The inner inlet 514a and outer inlet 514b are configured to receive a particle-laden solution that contains particles of various sizes, and may be connected to ports or other coupling devices (e.g., configured to mate with a syringe) to allow the solution to enter the spiral microfluidic separating system 510. In an alternative embodiment, only one inlet may be provided, or in another embodiment, more than two inlets may be utilized.

Figure 5B:
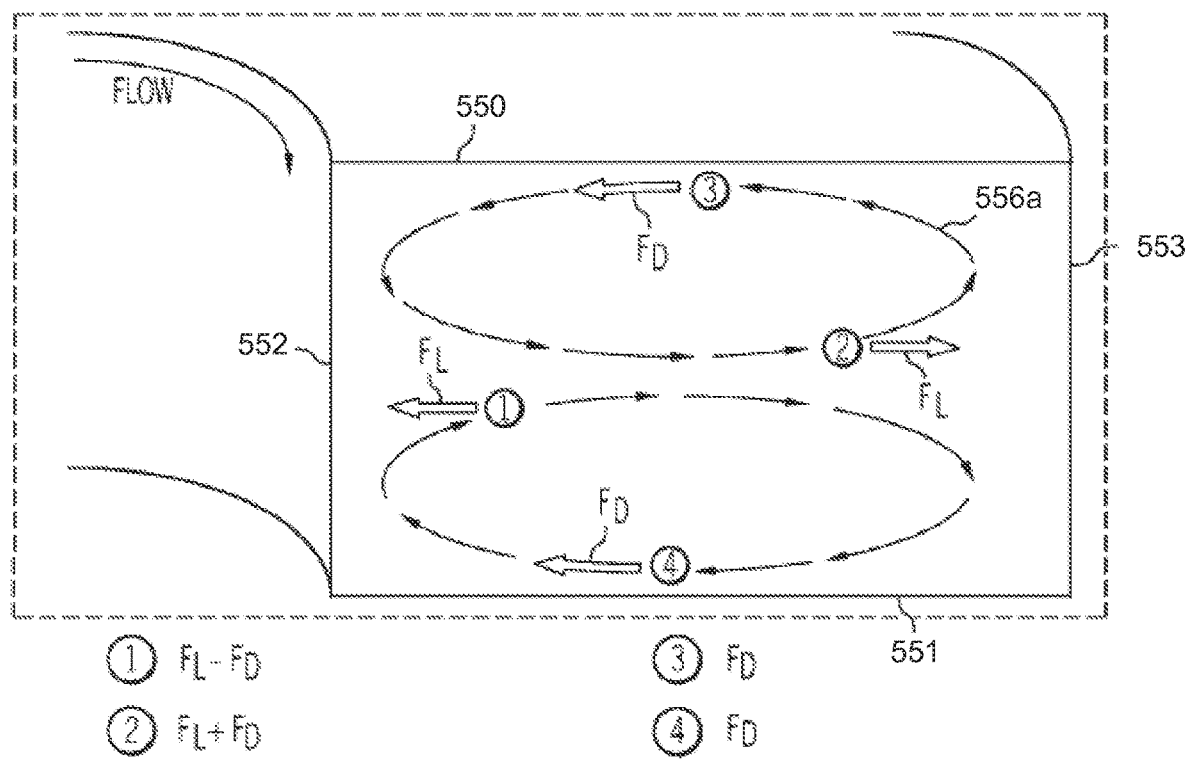
FIG. 5B schematically depicts a cross-section of an inner loop of the spiral microfluidic separating system depicted in FIG. 5A.

The inner inlet 514a and outer inlet 514b are fluidly coupled to a spiral fluid channel 511 that is arranged in a plurality of loops 511. FIG. 5B illustrates a cross-section view of the spiral fluid channel 511. The fluid channel 511 is rectangular in cross section, having two first walls 550, 551 and two second walls 552, 553. The first walls 550, 551 may be referred to herein as defining the width of the microchannel, while the second walls 552, 553 may be referred to herein as defining a height. However, no particular limitation is intended as to the orientation of the spiral microfluidic separating system 510.

The inner outlet 512a and outer outlet 512b are located at an opposite end of the spiral microchannel 511 from the inner inlet 514a and outer inlet 514b. As described in more detail herein, separated particles may be collected, detected, counted or otherwise analyzed at the inner and outer outlets 512a, 512b.

The design parameters of the spiral microfluidic separating system 510 may achieve a complete, or nearly complete, separation between two particle sizes using Dean drag to transpose smaller particles within the solution and inertial lift forces coupled with Dean drag to equilibrate larger particles within the solution. The combined effect of these forces results in the formation of distinct particle streams based on particle size, which in turn are collected at the inner outlet 512a and outer outlet 512b by taking advantage of the laminar flow in the spiral fluid channel 511.

FIG. 5B further illustrates forces acting upon particles flowing within the spiral fluid channel 511. Flow focusing in spiral channels requires a balance between inertial lift forces ($F_L$), which push particles away from a wall, and Dean drag ($F_D$), a force generated by a lateral, secondary-vortex flow along a spiral channel. The balance can be established for a given particle type when certain physical parameters of the flow are in specified ranges. The inertial lift forces ($F_L$) and Dean drag ($F_D$) can be calculated by $$F_D = 3\pi\mu U_{Dean} a_p \quad (1)$$

$$F_L = 0.05 \frac{a_p^4 \rho U_m^2}{D_h^2} \quad (2)$$

where $\mu$ is fluid viscosity, $U_{Dean}$ is average Dean velocity, $a_p$ is particle diameter, $U_m$ maximum fluid velocity, and $D_h$ is hydrodynamic diameter for a rectangular channel.

Thus, fluid flowing through the spiral fluid channel 511 experiences centrifugal acceleration directed radially outward leading to the formation of two counter-rotating vortices 556a, 556b known as Dean vortices in the top and bottom halves of the channel. Particles (labeled as particles 1-4 in FIG. 5B) flowing in a curvilinear channel experience a drag force due to the transverse Dean flows. Depending on particle size, this drag force ($F_D$) causes particles to move along the Dean vortices (i.e. circulate), and thus move towards either inner or outer channel wall. In addition to the Dean drag $F_D$, particles in a curvilinear channel experience pressure forces and inertial lift forces. The net lift force ($F_L$) acting on the particles is a combination of the shear-induced inertial lift force and the wall-induced inertial lift force. In Poiseuille flow, the parabolic nature of the velocity profile results in a fluidic shear-induced inertial lift force that acts on particles and is directed away from the microchannel center. As the particles move towards microchannel walls, an asymmetric wake induced around particles generates a wall-induced inertial lift force away from the wall. The magnitude of these opposing lift forces varies across the channel cross-section, with the wall-induced lift forces dominating near the channel walls (e.g., inner wall 552 and outer wall 553) and the shear-induced lift forces dominating near the center of the fluid channel 511. The particles thus tend to occupy equilibrium positions where the oppositely directed lift forces are equal and form narrow bands.

Figure 6A:
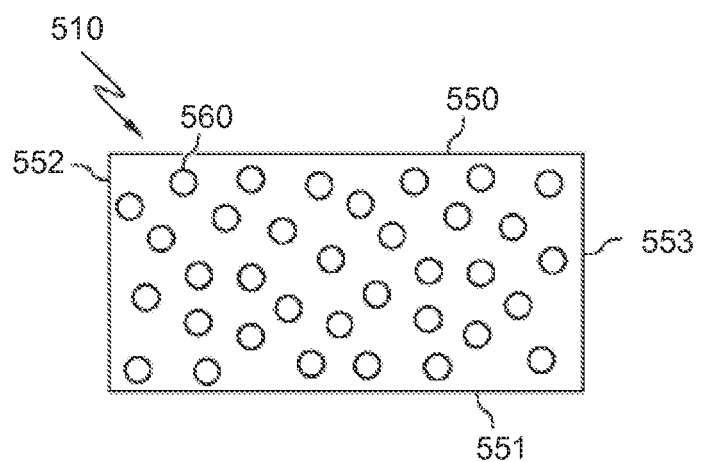
FIGS. 6A-6C schematically depict particle migration in the spiral microfluidic separating system depicted in FIG. 5A.
Figure 6B:
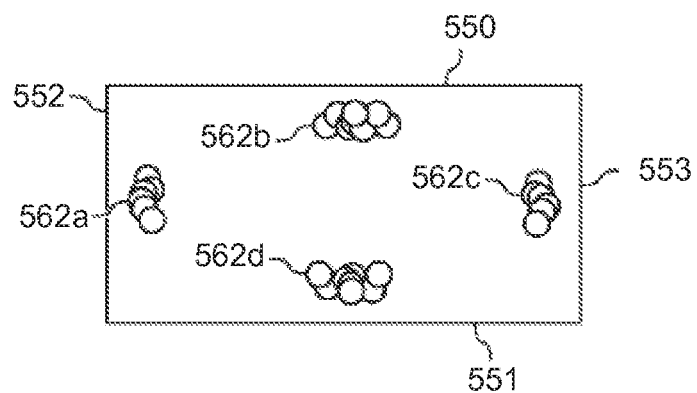
Figure 6C:
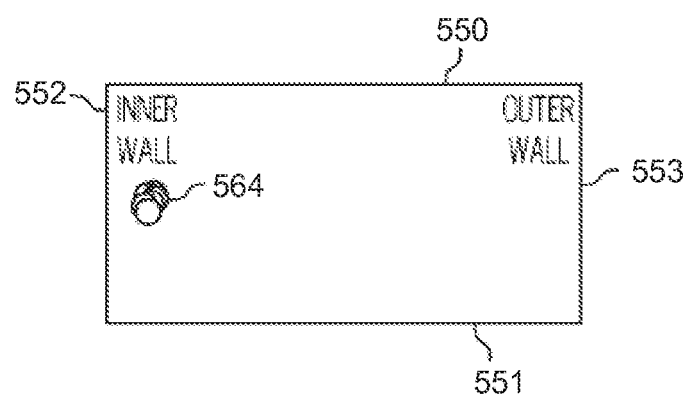

FIGS. 6A-6C schematically illustrate the principle of inertial migration. FIG. 6A illustrates particles 560 flowing within the microchannel 511. FIG. 6B illustrates that for a rectangular microchannel 511, the number of equilibrium positions where the shear-induced lift force and the wall-induced lift forces balance each other reduces to four at low Re (positions 562a, 562b, 562c, and 562d). As described in more detail below, adding a component of Dean drag ($F_D$) further reduces the four equilibrium positions to just one near the inner microchannel wall (position 564) illustrated in FIG. 6C.

Referring again to FIG. 5B, particles dispersed in the spiral fluid channel 511 get entrained in one of the two Dean vortices 556a, 556b that are formed at the top and bottom half of the fluid channel 511. The Dean drag force and the inertial lift forces tend to dominate the migration of neutrally buoyant particles flowing in microchannels at Re~1. Particles (illustrated by particle 3 and particle 4) flowing near the top and bottom fluid channel walls 550, 551 experience strong lateral flows due to Dean drag $F_D$ and are pushed towards the inner and outer microchannel walls 552, 553. Near the outer microchannel wall 553, the net lift force ($F_L$) acts along the direction of $F_D$ and the particles (particle 2) continue to follow the Dean vortices 556a, 556b independent of size. However, near the inner fluid channel wall 552, $F_L$ and $F_D$ act in opposite directions and depending on the magnitude of these forces, particles (particle 1) will either equilibrate and form a focused stream or continue to re-circulate in the Dean vortex.

The size dependence of the forces that act on particles flowing in spiral fluid channel, namely the Dean drag and the inertial lift forces, can be manipulated to produce a focused stream of particles of a similar size. The spiral geometry of the spiral microfluidic separating system 510 causes bigger particles to occupy a single equilibrium position near the inner fluid channel wall 552. On the other hand, smaller particles experience higher viscous drag due to the Dean flows and will continue to re-circulate along the Dean vortices 556a, 556b and can be transposed to the outer half of the microchannel 511. Thus, the spiral microfluidic separating system 510 uses inertial migration of larger particles and the influence of Dean drag on smaller particles to achieve a separation of different sized particles.

The length $L_f$ of the spiral microchannel 511 to achieve a complete separation of particles can be written as:

$$L_f = \frac{\pi \mu h^2}{\rho U_m a^2 f_L}, \qquad (3)$$

where μ is the viscosity of the fluid, h is the channel dimension (typically height), ρ is the density of the fluid, $U_m$ is the maximum velocity in the channel, a is the particle diameter, and $f_L$ is the particle lift coefficient.

Figure 7B:
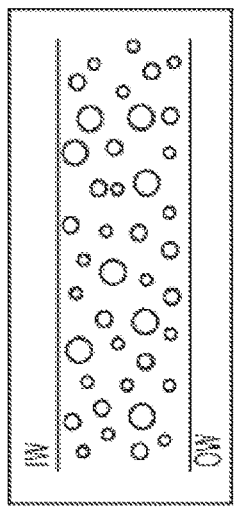
FIGS. 7A-7D schematically depict a spiral microfluidic separating system in accordance with an example of the present disclosure.
Figure 7C:
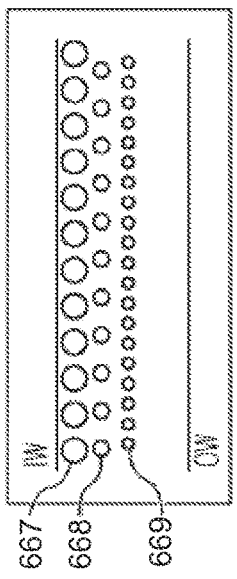
Figure 7D:
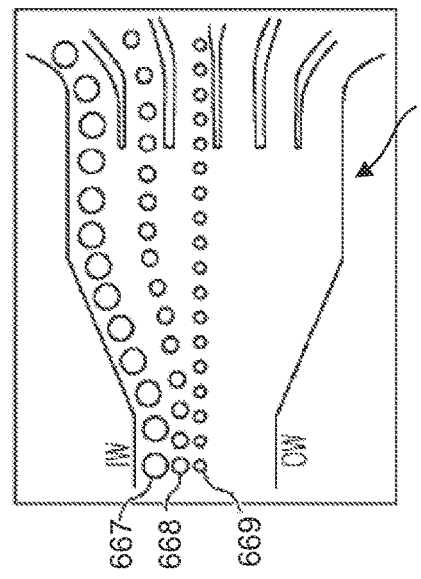
Figure 7A:
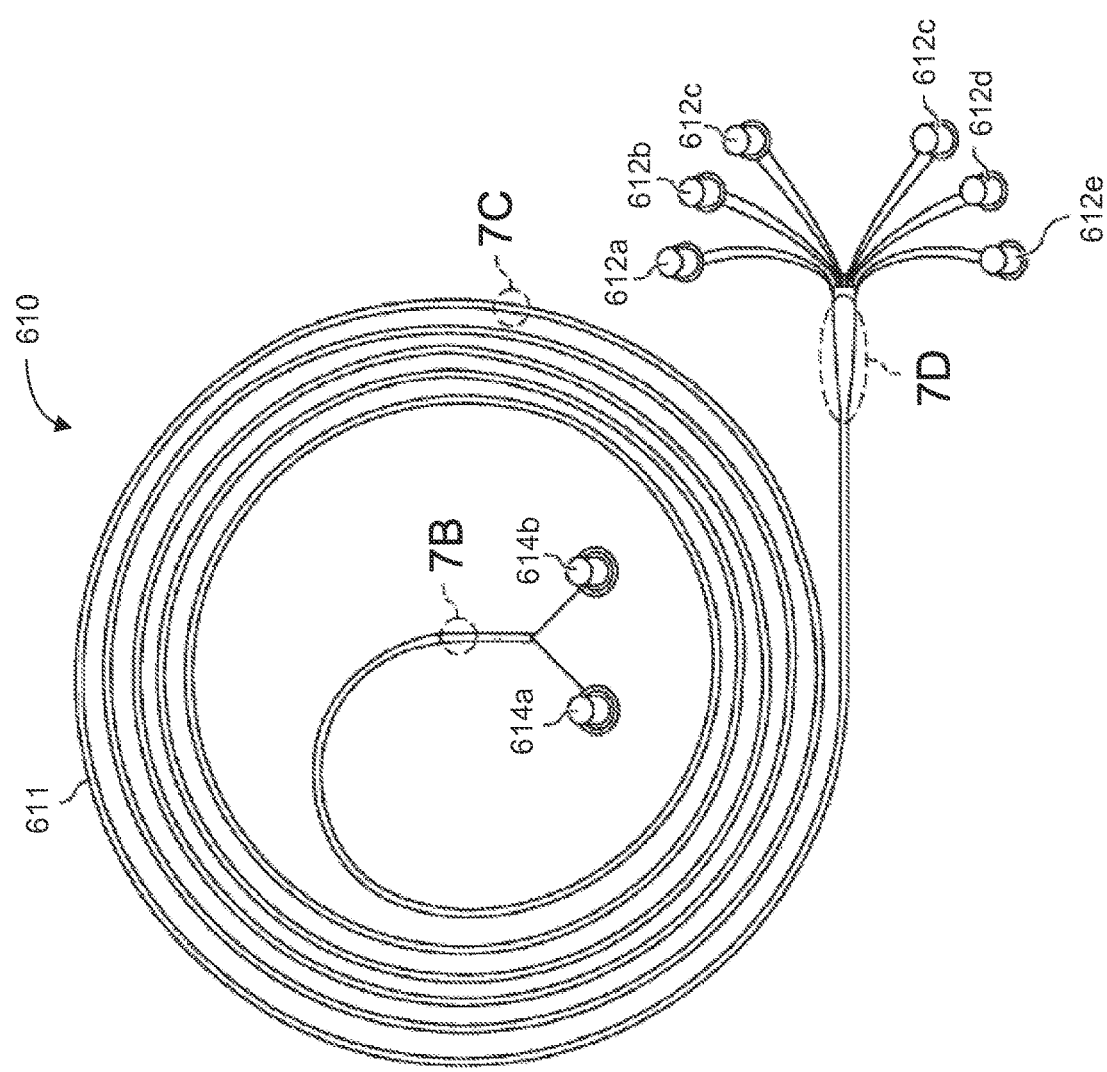

Referring now to FIGS. 7A-7D, another embodiment of the spiral microfluidic separating system 610 is illustrated. The exemplary spiral microchannel particle separator 610 comprises an inner inlet 614a, an outer inlet 614b, and six outlets 612a-f as illustrated in FIG. 7A. It should be understood that in some embodiments, only one inlet may be utilized. Alternatively, more than two inlets may be used. Further, more or fewer outlets may be present. The spiral microfluidic separating system 610 has a spiral fluid channel 611 that is arranged in a plurality of loops. In the illustrated embodiment, five loops are present from the inlets 614a, 614b to plurality of outlets 612a-f.

A combination of Dean drag and inertial lift forces result in particle equilibration at the inner fluid channel wall 652. The position at which the particles equilibrate is dependent on the ratio of these two forces. The geometric properties of the spiral microfluidic separating system 610 exploits the particle size dependence of the ratio of the two forces to form segregated, focused particles streams (illustrated by particle streams of particle sizes A, B and C of FIGS. 7C and 7D) that can be extracted by the outlets 612a-f. As illustrated in FIG. 7B, a particle-laden solution comprising particle sizes A, B and C (see FIG. 8) are introduced at the inner and/or outer inlets 614a, 614b. The particles of each size are co-mingled within the fluid channel 611. Within the spiral fluid channel 611, the particles begin to be focused into streams by particle size. As shown in FIG. 7C, particles of size A, which are the largest particles, are focused into a first stream 667 closest to the inner wall 652. Particles of size B, which is smaller than size A, are focused in a second stream 668 next to the stream of size A particles. Particles of size C, which is smaller than size B, are focused in an outer-most third stream 669.

A wide segment 664 may be located prior to the plurality of outlets 612a-f to aid in directing the streams of particles 667, 668, and 669 to the designated outlet. Separation between the individual particle streams is enhanced by the opening of the spiral fluid channel 611 into the wide segment 664 before extracting the individual streams at the plurality of outlets 612a-f. Referring to FIG. 7D, the plurality of outlets 612a-f are arranged to receive the focused streams of particles. First particle stream 667 comprising the larger particles of size A exits the spiral microfluidic separating system 610 at outlet 612a, second particle stream 668 comprising the particles of size B exits the spiral microfluidic separating system 610 at outlet 612b, and the smallest particles of size C exits the spiral microfluidic separating system 610 at outlet 612c.

Figure 8:
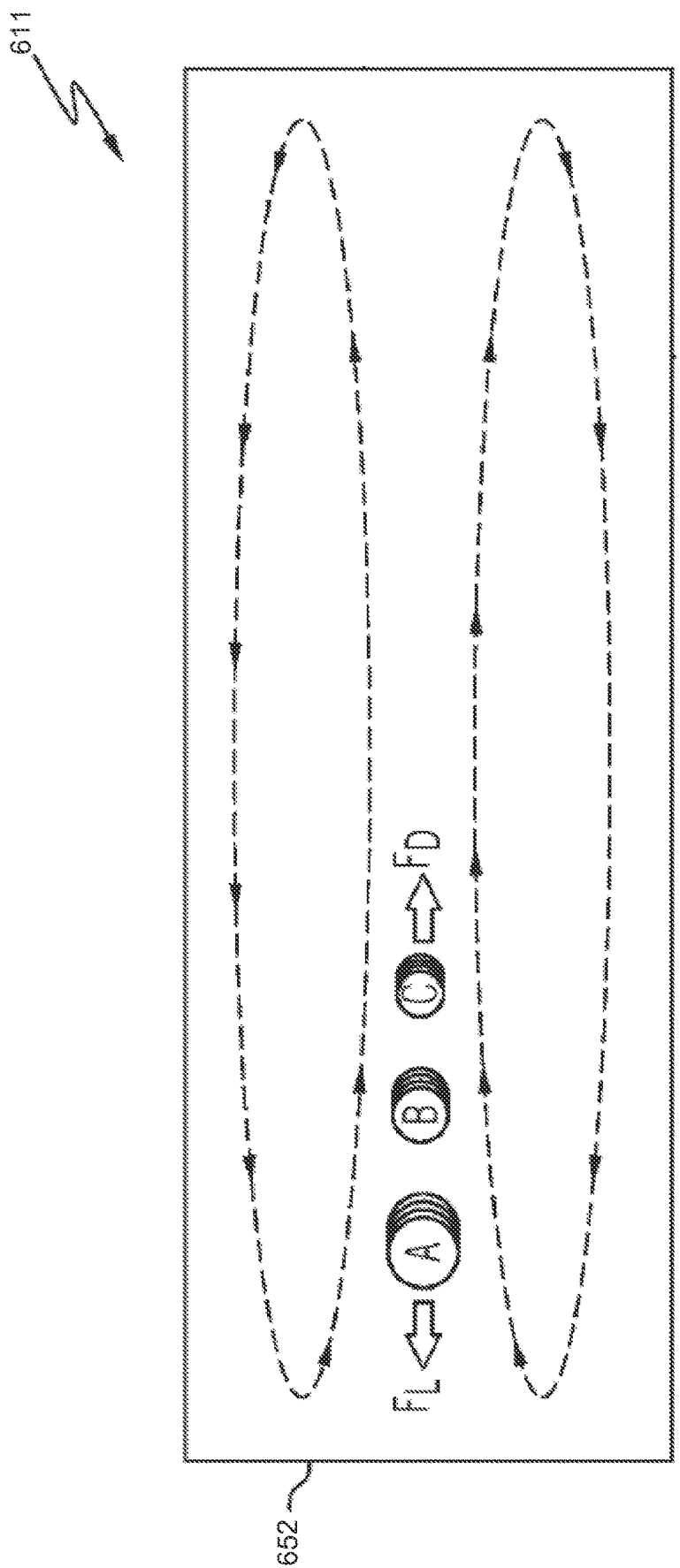
FIG. 8 schematically depicts a cross-section of an inner loop of the spiral microfluidic separating system depicted in FIGS. 7A-7D.

FIG. 8 illustrates a fluid channel 611 cross section and the effects of $F_L$ and $F_D$ on particles. The ratio of forces ($F_L/F_D$) is the determining factor in where a particle of a given size (diameter) equilibrates (e.g., within streams or particles sizes A, B, or C). The dominant inertial lift forces align the randomly distributed particles at the inlet near the inner fluid channel wall as the flow progresses downstream. On the other hand, the significant Dean drag force move these focused streams farther away from the channel wall depending on the particle size, with the largest particle being closest to the inner channel wall. This results in the evolution of three distinct particle streams which can be independently extracted by designing appropriate outlets.

As described above, the fluid channel of a microfluidic separating system can comprise a spiral configuration to sort material based on inertial microfluidics. Inertial microfluidics forces balance flow and lift to focus particles in a spiraling channel and expected to direct cells, based on size and shape to different channel outlets. Thus, use of spiral channels with appropriate geometries and flow rates can be used to separate and concentrate sperm cells from other cells in a mixture. As cells and particles move through the spiral channels, a counter rotating flow is established that causes particles to move laterally in the channel. As they move towards the side walls of the channel, lift forces pushing the particles away from the wall cause the particles to move to an equilibrium position in the channel that balances the flow and lift forces. The location of this equilibrium position for particles in the channel depends on the size of the particles, their shape, the flow rate, and the geometry of the spiral channels. For a given channel geometry, particles of different size and shape will focus at different locations in the channel. By optimizing the channel geometry and flow rate, conditions can be determined where sperm will separate and be concentrated relative to the various other particles in the sample. Note that sperm have both a unique size and shape, which should provide good opportunities for using these methods for purification. As a spiral channel is introduced, the lift and focusing locations are strongly affected by the radius of the spiral. Thus, by working with these various parameters, an optimal channel and flow rate for sperm cell separation from contaminating cells can be determined.

Using these theoretical principles discussed above, a spiral fluid channel can be designed to effectively separate sperm. For focusing, the ratio ($R_f$) between inertial lift forces, and Dean drag, is given by $$R_f = \frac{F_L}{F_D} \geq \sim 0.08. \qquad (4)$$

can be greater than or equal to 0.08, which makes the Dean drag (eq. 1) dominant. For strong focusing, the particle/channel dimension ratio (λ), given by $$\lambda = \frac{a_p}{D_h} \geq 0.07 \qquad (5)$$

can be greater than or equal to 0.07. The aspect ratio of the channel can be between ~1:2 and ~1:4 (height:width or width:height). The length of the spiral channel can be greater than about $2L_f$ (eq. 3) to ensure a good separation of particles.

In one aspect, the fluid channel can have a height from about 25 μm to about 100 μm. In another aspect, the fluid channel can have a width from about 50 μm to about 400 μm. In yet another aspect, the aspect ratio of the channel can be from about 0.2 to about 0.5. In still another aspect, an average radius of the spiral can be from about 1 cm to about 16 cm in a geometric progression. In a further aspect, the flow rate in the fluid channel can be from about 0.1 mL/min to about 1 mL/min or higher for the larger channels. The number of outlets can be from 2 to 10, although the fluid channel can have any suitable number of outlets. In a particular example, a spiral channel can have an initial radius of 0.7 cm, a final radius of 0.899 cm, a channel width of 150 μm, a channel height of 50 μm, 4 spiral turns, and a space between channels of 310 μm. One challenge of designing a microfluidic separating system for separating sperm is the irregular shape of sperm cells (approx. sperm head length of 4.79 μm and width of 2.82 μm), while the theory assumes spherical particles. As one estimate, sperm can be considered to be 5 μm diameter spheres. For resolution estimates, red blood cells can be approximated as 9 μm diameter spheres (RBC dimensions: diameter of 7.5~8.7 μm and thickness of 1.7~2.2 μm).

A microfluidic separating system in accordance with the present disclosure can therefore be based on inertial microfluidic approaches that rely on cell size and shape. Sperm may exhibit unique behavior when compared to cells of a similar size using inertial microfluidic channels because of their long tails, which should aid in their rapid purification and collection. Thus, spiral channels can be used to separate immotile sperm from red blood cells and other contaminating cells. In one aspect, separation techniques can focus on sperm size and/or shape characteristics. For example, an inertial microfluidic design can take advantage of the "sail-like" shape properties of a sperm tail to flow them in a specific direction.

Figure 9:
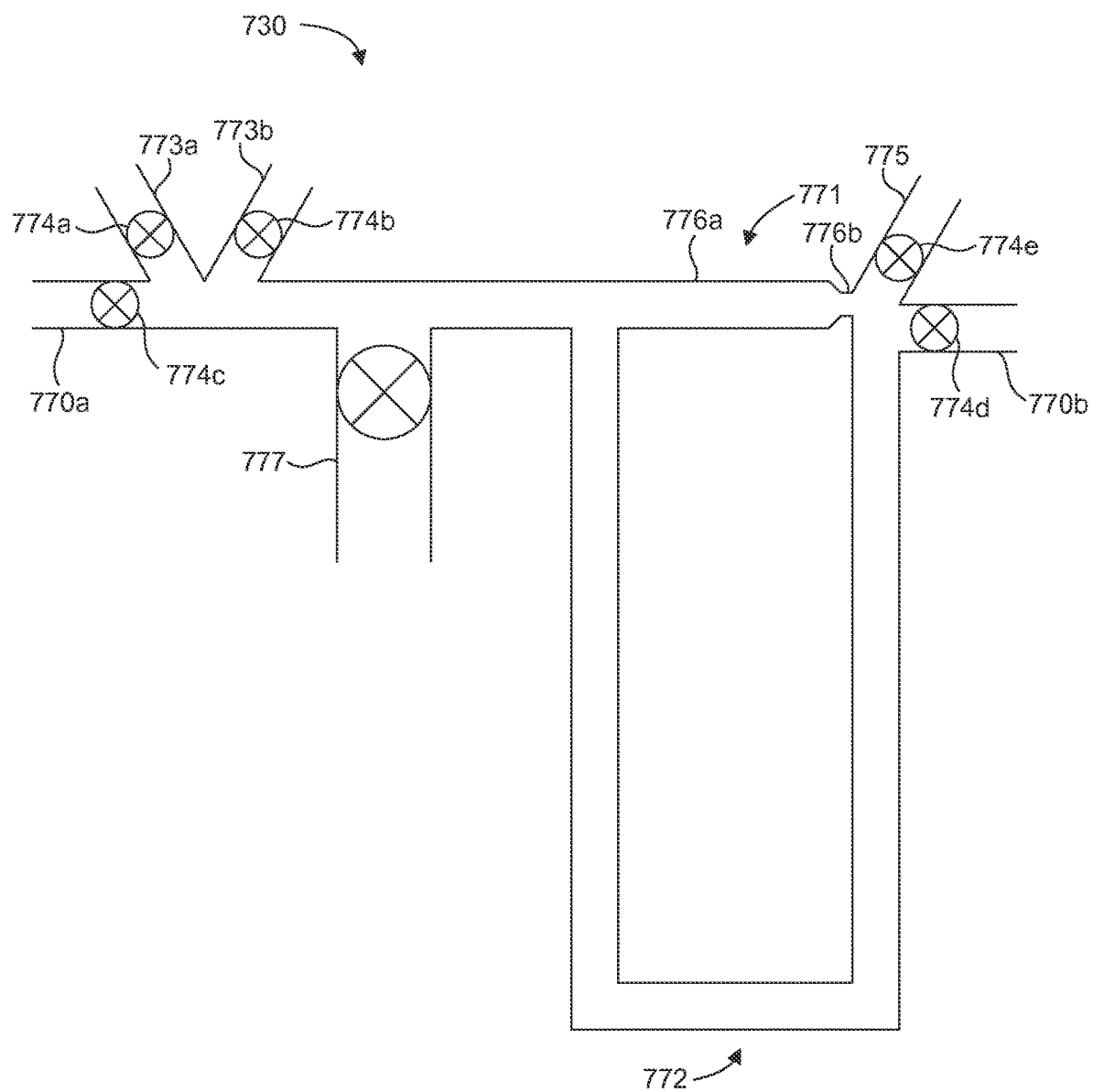
FIG. 9 is a schematic illustration of a sorting/concentrating system in accordance with an example of the present disclosure.

FIG. 9 schematically illustrates a sorting/concentrating system 730 in accordance with an example of the present disclosure. The sorting/concentrating system 730 can include an inlet 770 to receive tissue sample material from a microfluidic separating system as disclosed herein, and an outlet 770b. The sorting/concentrating system 730 can also include a first fluid conduit 771 and a second fluid conduit 772. The first fluid conduit 771 can be sized or configured to prevent passage of a given size particle (e.g., a cell of a desired size fraction of the tissue sample material) through the conduit. In one aspect, the first fluid conduit 771 can have a trap portion 776a sized to receive or accommodate one or more particles of the desired size, and a reduced size portion 776b (~1.5 μm wide for sperm) configured to prevent passage of the particles through the first conduit. A fluid resistance of the first fluid conduit 771 can be greater than a fluid resistance of the second fluid conduit 772 such that the given size particle flows toward the first conduit and is trapped at the first conduit. In addition, the sorting/concentrating system 730 can include a plurality of aliquot storage channels 773a, 773b (i.e., immobilization channels) and a plurality of valves 774a, 774b associated with the plurality of aliquot storage channels to facilitate separation of aliquots into the aliquot storage channels for storage (e.g., cryopreservation). A back-flow line 775 can be included to provide fluid for flushing trapped particles from the first conduit 771 and into the aliquot storage channels 773a, 773b. The inlet, the outlet, and the back-flow line 775 can include valves 774c-e, respectively, to facilitate operation of the sorting/concentrating system 730. A valved conduit 777 can be included to control flow.

Figure 10A:
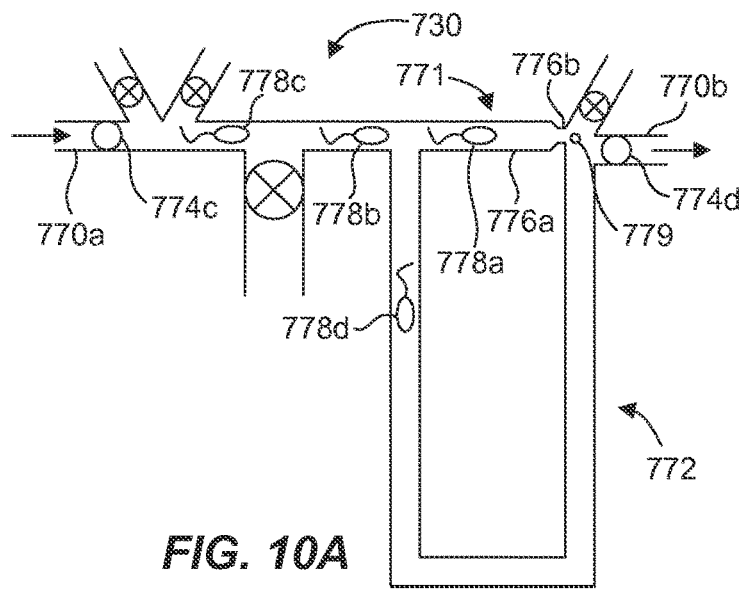
FIGS. 10A-10C illustrate the sorting/concentrating system of FIG. 9 in operation in accordance with an example of the present disclosure.
Figure 10B:
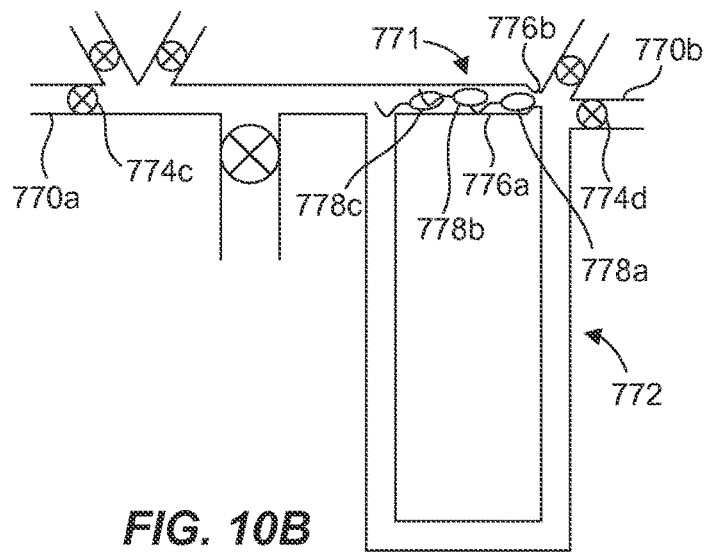
Figure 10C:
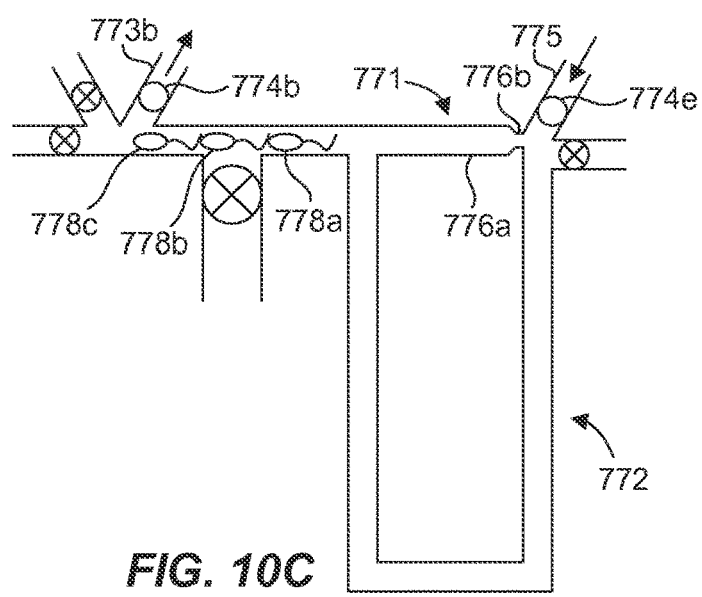

FIGS. 10A-10C illustrate the sorting/concentrating system 730 in operation. FIG. 10A shows the valve 774c of the inlet 770a and the valve 774d of the outlet 770b open to allow tissue sample material to flow into the system. All other valves are closed. In this case, the tissue sample includes sperm 778a-d, which are desired to be concentrated and sorted. Tissue sample material will either flow into the first conduit 771, where there is a trap for larger particles, or into the second conduit 772, bypassing the trap. However, due to the higher resistance in the second conduit 772, the material in the tissue sample preferentially flows into the first fluid conduit 771. Large particles, such as the sperm 778a-c become trapped in the first conduit 771 by the reduced size portion 776b (see FIG. 10B), while a small particle 779 can pass through the reduced size portion 776b of the first conduit 771 and thus exit the system 730 via the outlet 770b. Any particles, including large particles (e.g., sperm 778d), which do not flow into the first conduit 771 can bypass the trap. Providing two flow paths ensures that as the sperm 778a-d move through the system 730, they become trapped or bypass the trap. The second conduit 772 can be adjusted in length and/or cross-section area in order to obtain a desired flow resistance (i.e. back pressure). Although design parameters may vary, as a general guideline, the second conduit can have a flow resistance which is from 0.3 to 3 times greater than the first conduit. In one aspect, the trap portion 776a of the first conduit 771 and the bypassing aspect can be configured to trap a desired number of sperm in a single trap, such as from about 1 to about 5. Once a desired number of sperm have been trapped, the inlet and outlet valves 774c, 774d can be closed, as shown in FIG. 10B, to stop flow through the system 730. As shown in FIG. 10C, the valve 774e of the back-flow line 775 and the valve 774b of the aliquot storage channel 773b can be opened to flush the sperm 778a-c from the trap portion 776a of the first channel 771 and into the aliquot storage channel 773b. Alternately, the valve 774a of the aliquot storage channel 773a can be opened and the valve 774b closed to direct sperm into the aliquot storage channel 773a. The valves 774a, 774b can be alternately opened during a single flush to split some portion of trapped sperm into the aliquot storage channels 773a, 773b, or the valves 774a, 774b can be opened alternately with each flush cycle. Thus, the sorting/concentrating system 730 can remove undesired particles from a tissue sample, thus concentrating the sperm, and sort sperm into aliquots for cryopreservation. Although only two storage aliquot channels are illustrated, it should be recognized that the system 730 can include any suitable number of storage aliquot channels and associated valves to route trapped sperm in predefined locations. For example, sperm can be lined up and then dispensed one at a time into individual wells of a plate. In one aspect, the sorting/concentrating system 730 can be configured as a "chip" that incorporates only a single trap.

It should be recognized that the sorting/concentrating system 730 can be configured as a concentrating system, which may or may not be utilized as a sorting system, simply by omitting one, or using only one, of the aliquot storage channels. Similarly, the sorting/concentrating system 730 can be configured as a sorting system, which may or may not be utilized as a concentrating system, simply by only operating the valves 774a-c of the inlet 770a the aliquot storage channels 773a, 773b.

Figure 11:
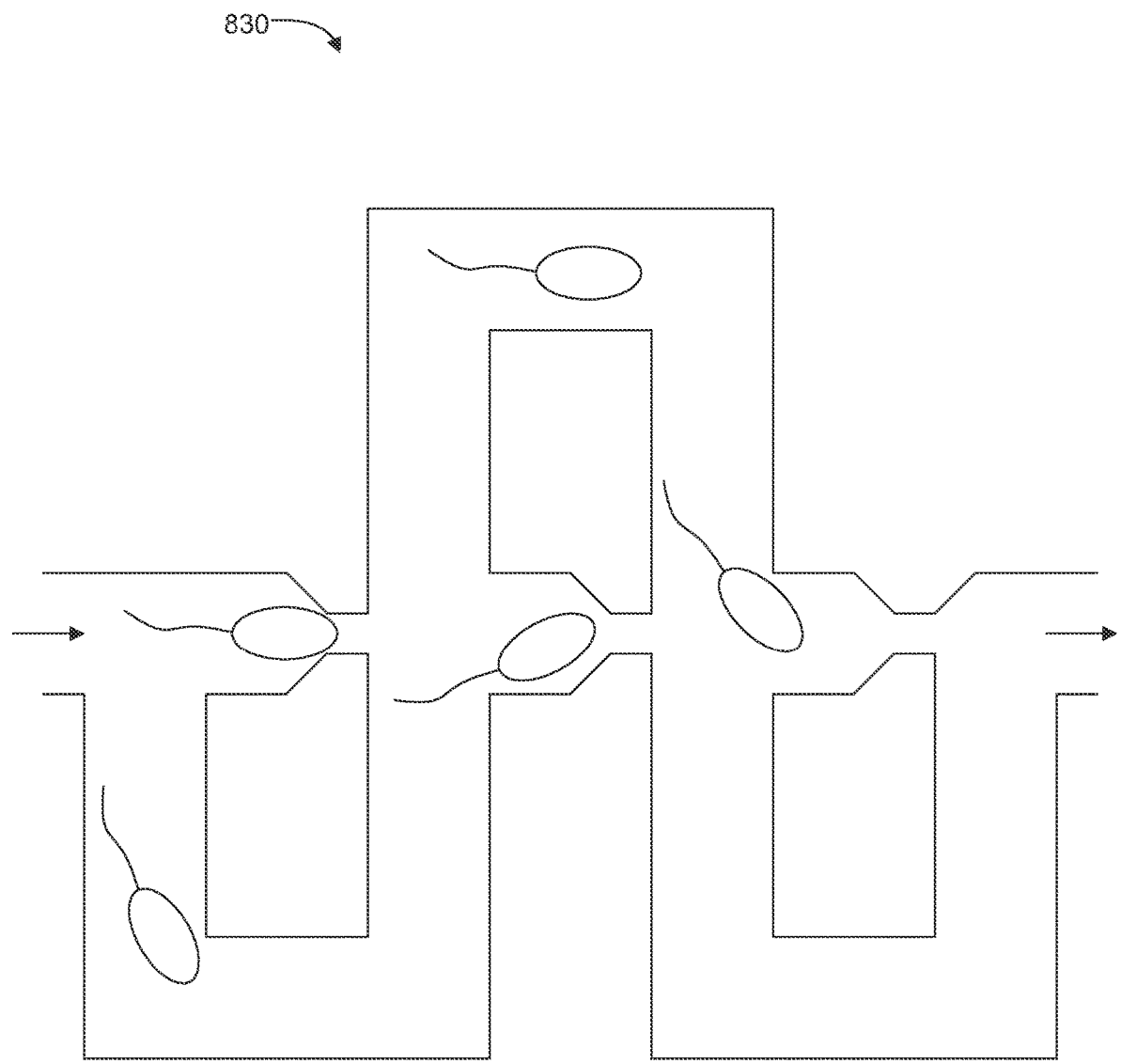
FIG. 11 is a schematic illustration of a sorting/concentrating system in accordance with another example of the present disclosure.

FIG. 11 schematically illustrates a sorting/concentrating system 830 in accordance with another example of the present disclosure. The sorting/concentrating system 830 is similar in many respects to the sorting/concentrating system 730 of FIG. 9 in that it incorporates a trap and bypass configuration. In this case, however, the sorting/concentrating system 830 includes multiple traps and bypasses in series. Although valves are not shown in this example, it should be recognized that the sorting/concentrating system 830 can include valves in any suitable arrangement to facilitate trapping of relatively large particles, such as sperm, and retrieval of the large particles from the system 830 in a manner consistent with that discussed above, such as by sequential valving and back-flushing to remove the sperm from the traps.

The components disclosed herein may be fabricated of a suitable material such as, but not limited to, poly-dimethylsiloxane (PDMS) material, polymethylmethacrolate (PMMA), polycarbonate (PC), and/or cyclic olefin copolymer (COC).

In one aspect, the technology disclosed herein is a single tissue sample processing system that can be used for isolation and enrichment of sperm over somatic cells and debris where the sample source is testicular tissue. In another aspect, the tissue sample processing system can also enable aliquoting of sperm sample for cryopreservation and use in downstream applications. Other capabilities include cultivating sperm and separating sperm based on ploidy.

Further applications of the technology disclosed herein exist in the fields of clinical assisted reproductive technologies (ART) for humans and animals, and in reproductive research. Current ART related sperm separation technologies rely on sperm motility for separation, and because of this, typical separation approaches are not often applied to ART, whereas the approach disclosed herein does not require motile cells and is a unique approach in the ART field. For example, a tissue sample processing system as disclosed herein, which can enrich small populations of cells from testicular tissue specimens, has broad implications for applications in the field of male infertility. The tissue sample processing system can not only to isolate viable sperm, but can also isolate other sparse cell types, such as spermatogonial stem cells and other sperm precursors. This is significant because current methods for isolation of spermatogonial stem cells from human testicular tissue involve the use of agents, such as antibodies, that are not compatible with therapeutic procedures. Importantly, the tissue sample processing system can isolate these cell types without the addition of harmful reagents. In conjunction with in vitro spermatogonial stem cell differentiation techniques, the tissue sample processing system could be used to culture mature sperm cells, thus providing fertility treatment options to patients that currently produce no mature sperm.

The present technology can also be used to select individual sperm for use in IVF. For example, the tissue sample processing system may be used to separate normal euploid sperm cells, which comprise exactly one of each chromosome, from aneuploid sperm cells, which contain too few or too many of one or more chromosome. The ability to isolate euploid sperm based on mass or charge for IVF would increase the likelihood of producing viable embryos, and decrease the likelihood of monosomic or trisomic embryos. Besides isolating euploid sperm, atraumatic preservation of individual sperm may enable non-invasive imaging to determine the reproductive potential of each sperm, allowing embryologists to select the sperm with the best potential for successful fertilization and live birth.

In addition to clinical purposes, isolation and cryopreservation of individual testicular cell types from small tissue volumes can improve reproductive research capabilities. For example, NOA patients often exhibit specific foci of spermatogenesis within the testes, and it is currently unclear what promotes spermatogenesis in one seminiferous tubule but not another. Isolation of specific cell subpopulations from seminiferous tubules would allow gene expression, epigenetic, or other molecular analyses to be performed, potentially elucidating the molecular mechanisms that dictate spermatogenesis. Isolation of spermatogonial stem cells would also enable researchers to study the process of pluripotent conversion in human tissue to compliment cutting-edge research in mouse tissues. Furthermore, capturing individual sperm cells may allow researchers to study the characteristics individual sperm as opposed to studying bulk heterogeneous sperm populations.

In accordance with one embodiment of the present invention, a method of separating sperm cells is disclosed. The method can comprise obtaining a microfluidic separating system having a fluid channel and a plurality of outlets. The method can further comprise disposing a carrier fluid in the fluid channel. Additionally, the method can comprise disposing a sperm sample in the fluid channel, wherein flow of the carrier fluid and the sperm sample in the fluid channel facilitates segregation of materials in the sperm sample based on size into a plurality of size fractions, such that each one of the plurality of outlets receives a different size fraction of the materials in the sperm sample.

In one aspect of the method, the fluid channel comprises a spiral configuration. In another aspect of the method, the microfluidic separating system can comprises an inlet zone having a carrier fluid inlet to receive the carrier fluid and a tissue sample inlet to receive the tissue sample, an outlet zone having the plurality of outlets, and a transport region between the inlet zone and the outlet zone, the transport region being open to the carrier fluid and the tissue sample, wherein a cross-flow in the transport region facilitates segregation of the materials in the tissue sample based on size. In yet another aspect of the method, the material in the sperm sample associated with at least one of the plurality of outlets comprises non-motile sperm cells. In one aspect, the method can further comprise associating a sorting system with at least one of the plurality of outlets, wherein the material in the sperm sample associated with the at least one of the plurality of outlets comprises non-motile sperm cells, and sorting the non-motile sperm cells into a plurality of aliquots. In one aspect of the method, the sorting system can comprises an inlet to receive the material in the tissue sample associated with the at least one of the plurality of outlets, a plurality of aliquot storage channels, and a plurality of valves associated with the plurality of aliquot storage channels to facilitate separation of the plurality of aliquots into the aliquot storage channels.

In accordance with another embodiment of the present invention, a method of separating non-motile sperm cells from a sperm sample is disclosed. The method can comprise flowing a sperm sample through a fluid channel under laminar flow conditions, wherein a cross-flow in the fluid channel facilitates segregation of non-motile sperm cells within an inner fluid flow layer. Additionally, the method can comprise spatially separating the inner fluid flow layer.

In one aspect of the method, the fluid channel can comprise a spiral configuration. In one aspect, the method can further comprise receiving the non-motile sperm cells in an outlet of the fluid channel. In another aspect, the method can further comprise sorting the non-motile sperm cells into a plurality of aliquots. In one aspect of the method, each of the plurality of aliquots can comprise from about 1 to about 20 non-motile sperm cells. In another aspect of the method, each of the plurality of aliquots can comprise from about 1 to about 10 non-motile sperm cells. In yet another aspect of the method, each of the plurality of aliquots can comprise a single non-motile sperm cell.

It is noted that no specific order is required in the methods disclosed herein, though generally in one embodiment, method steps can be carried out sequentially.

Figure 12A:
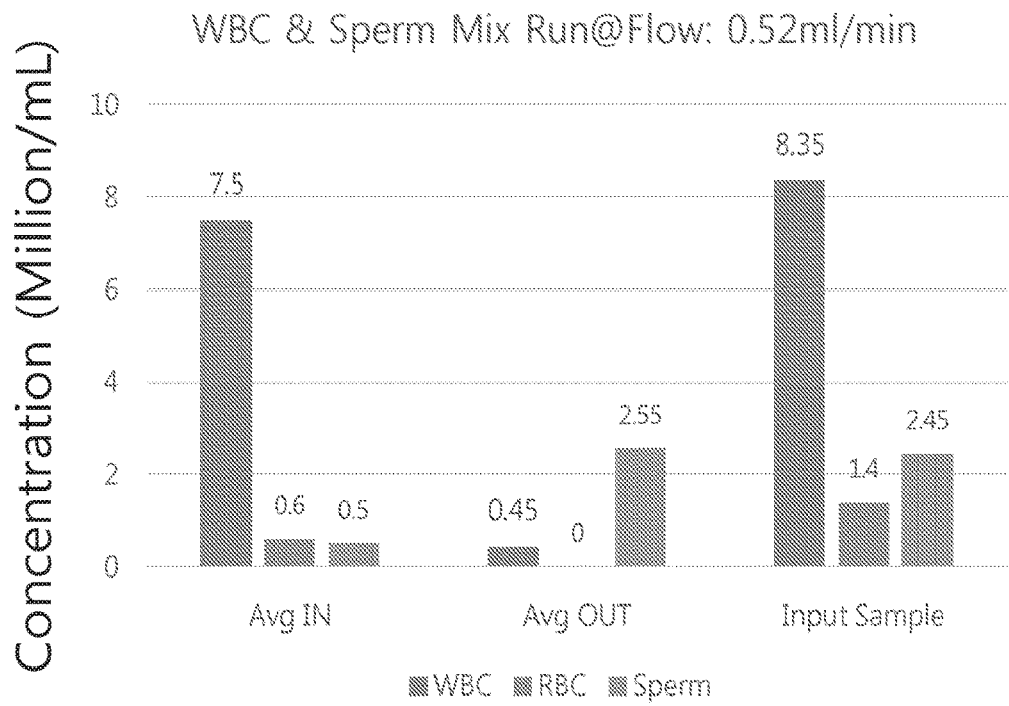
FIGS. 12A through 22 illustrate test data related to performance of a tissue sample separation device in accordance with one aspect of the invention.
Figure 12B:
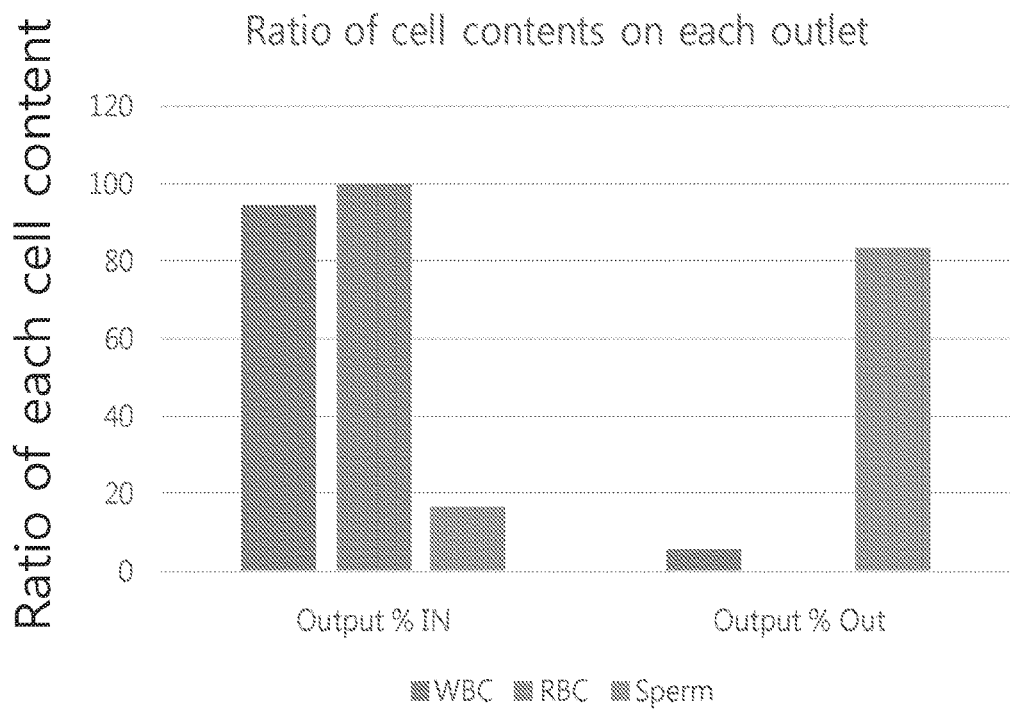
Figure 13:
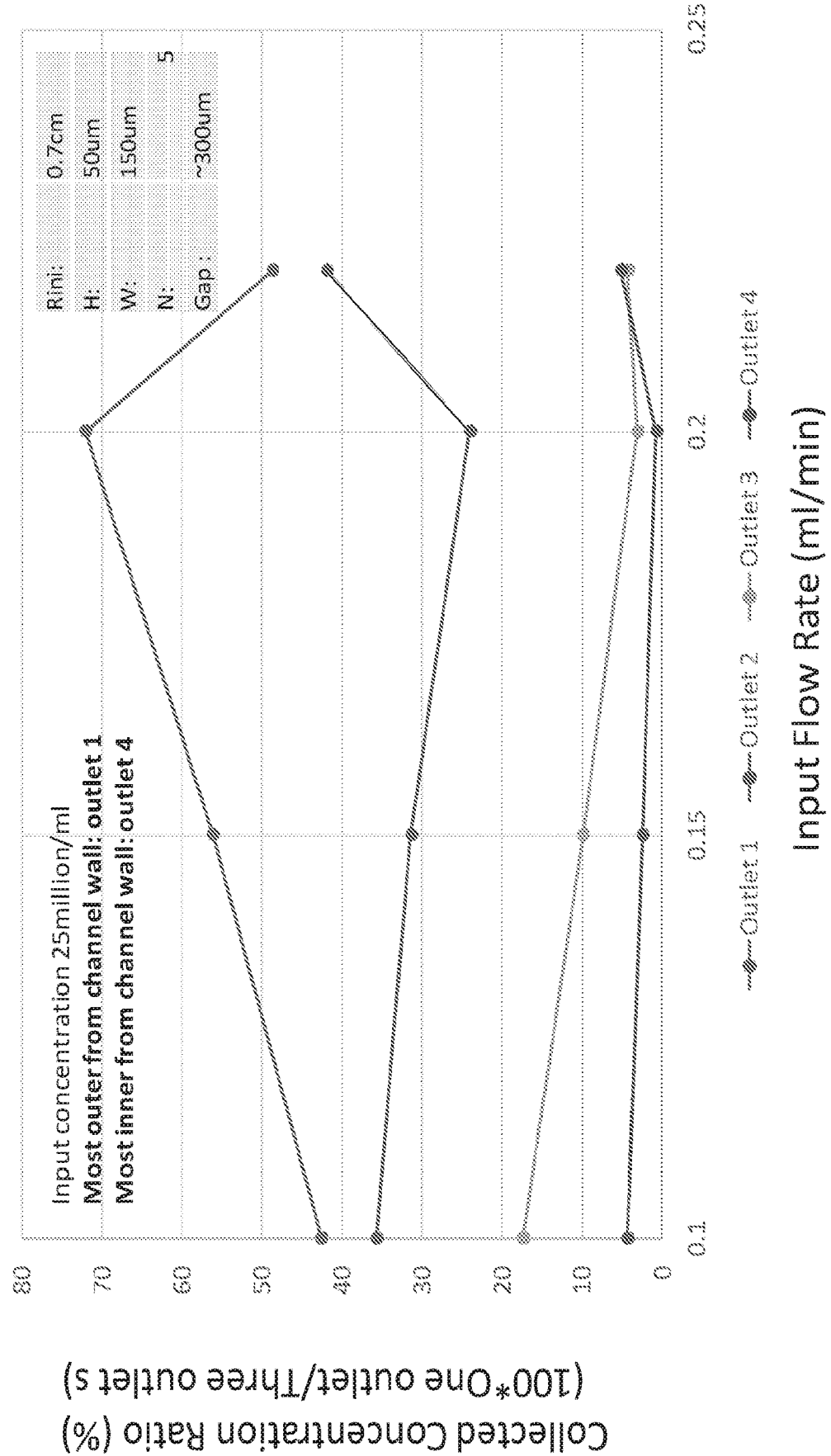
Figure 14:
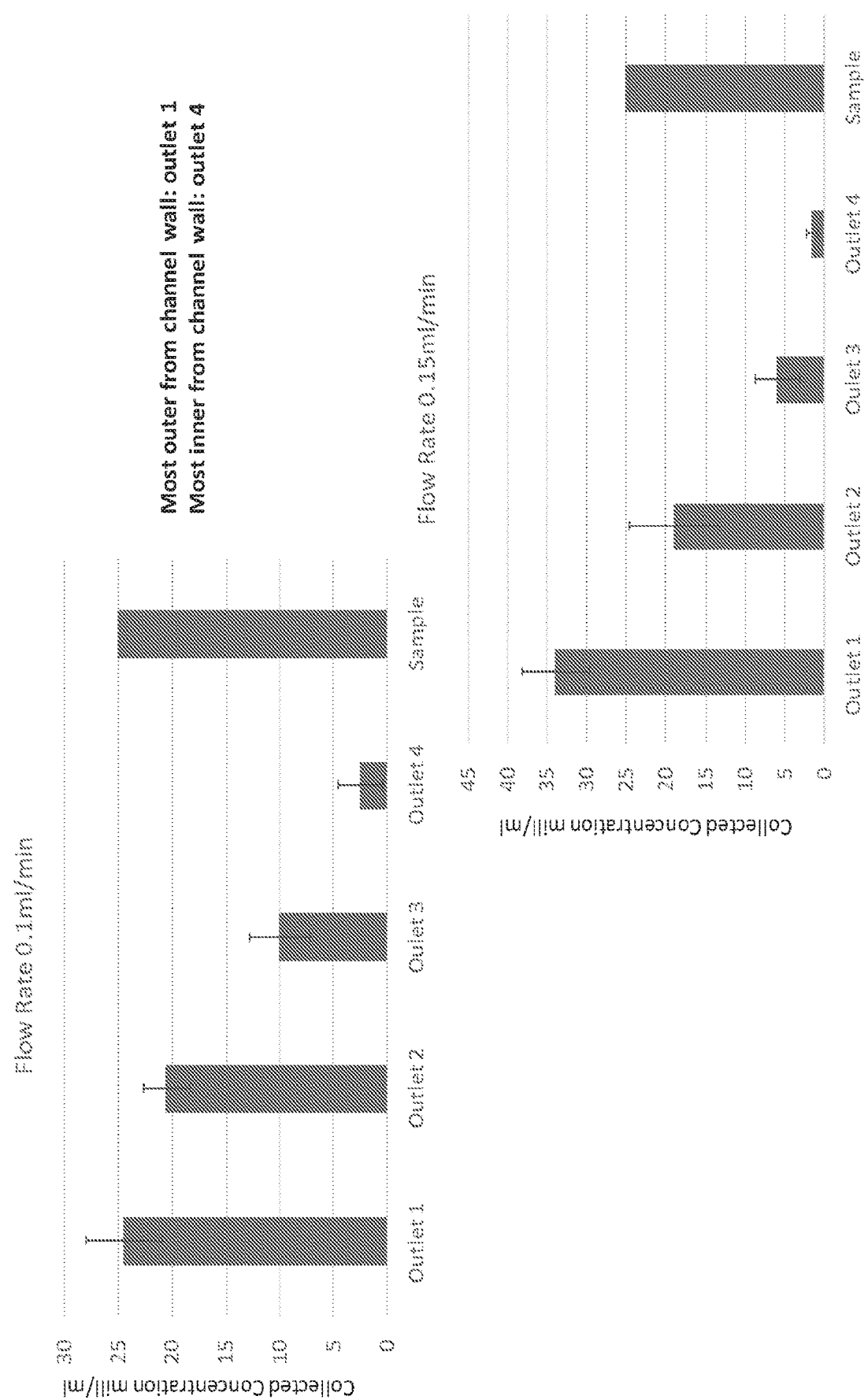
Figure 15:
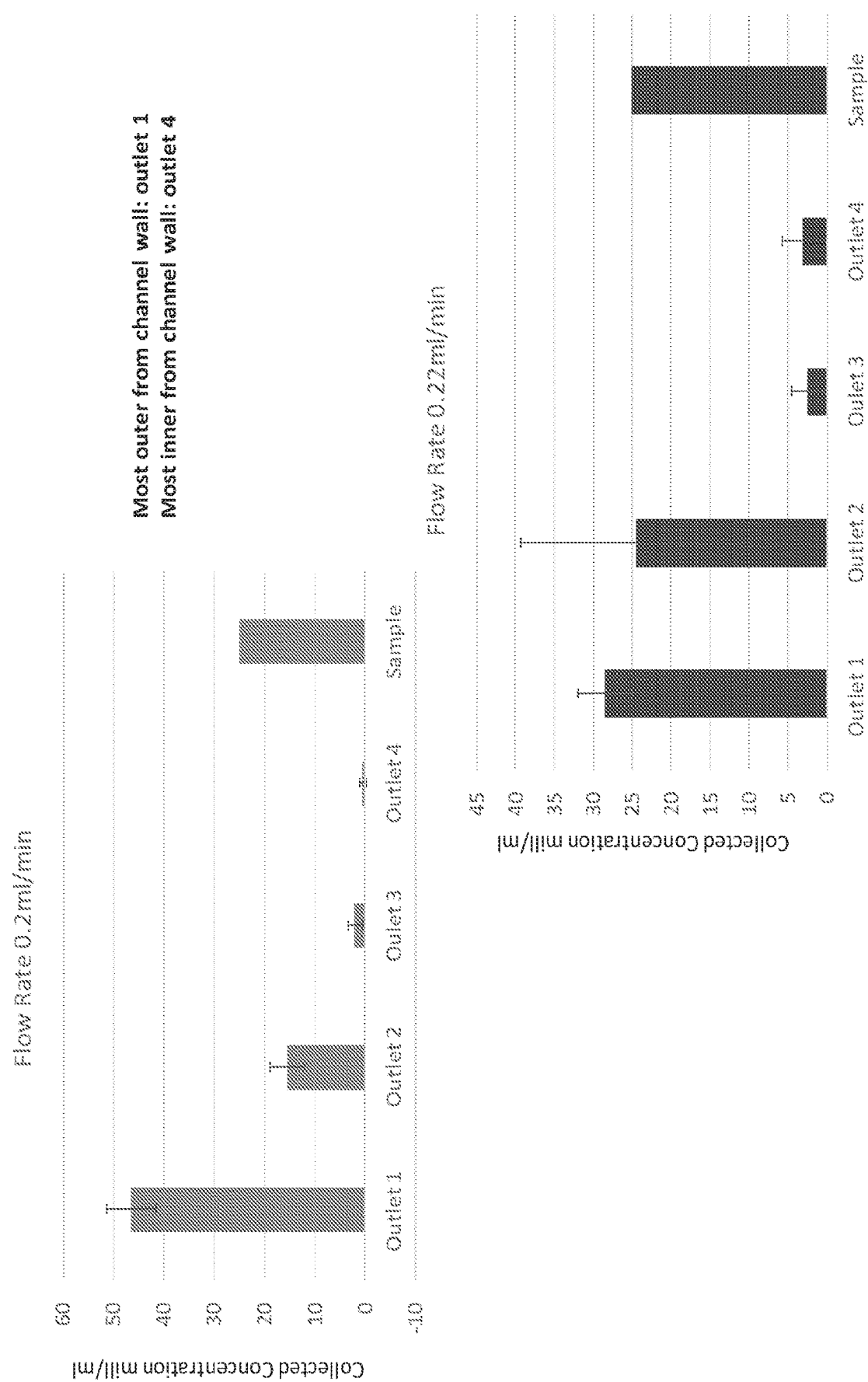
Figure 16:
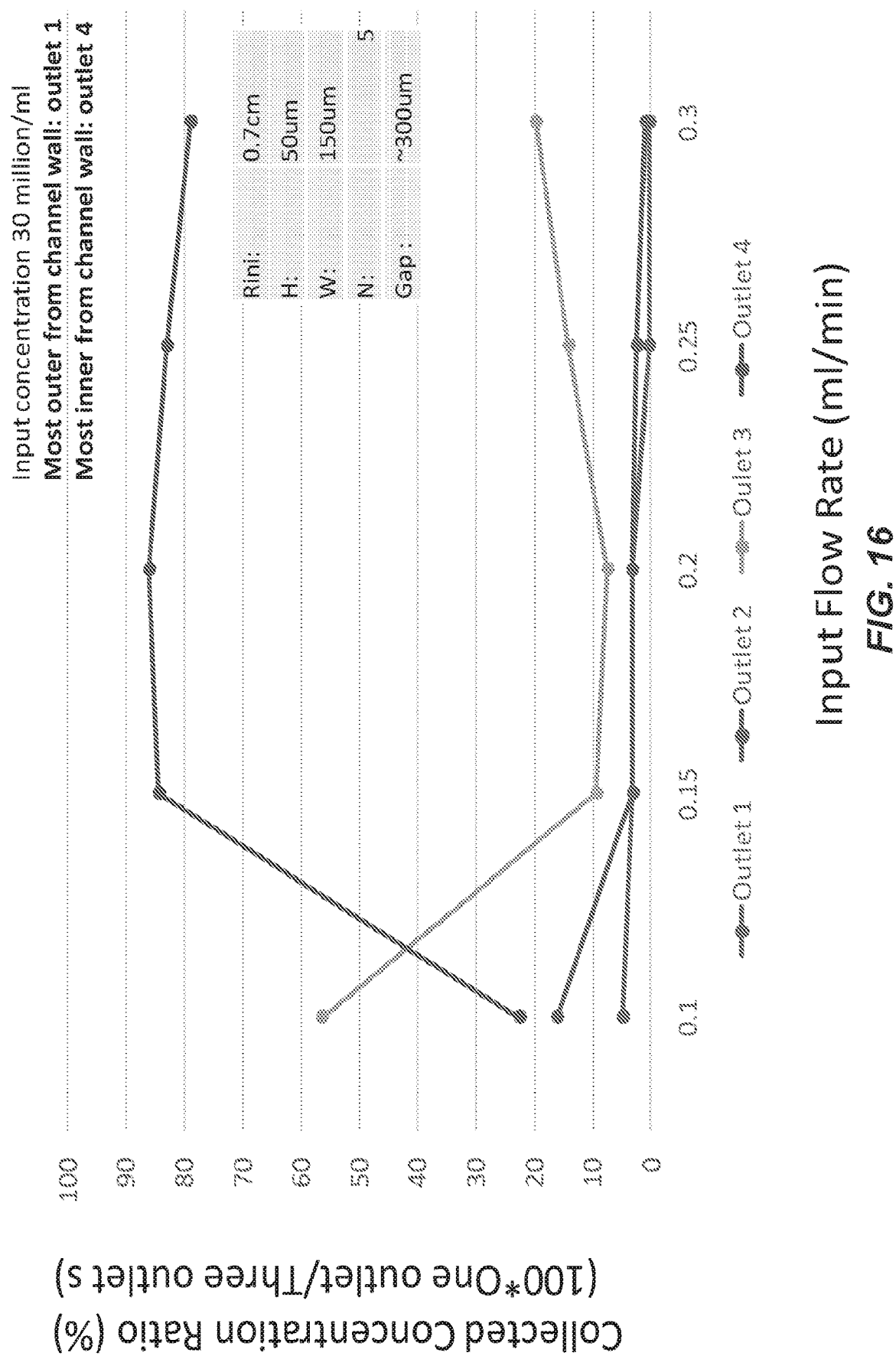
Figure 17:
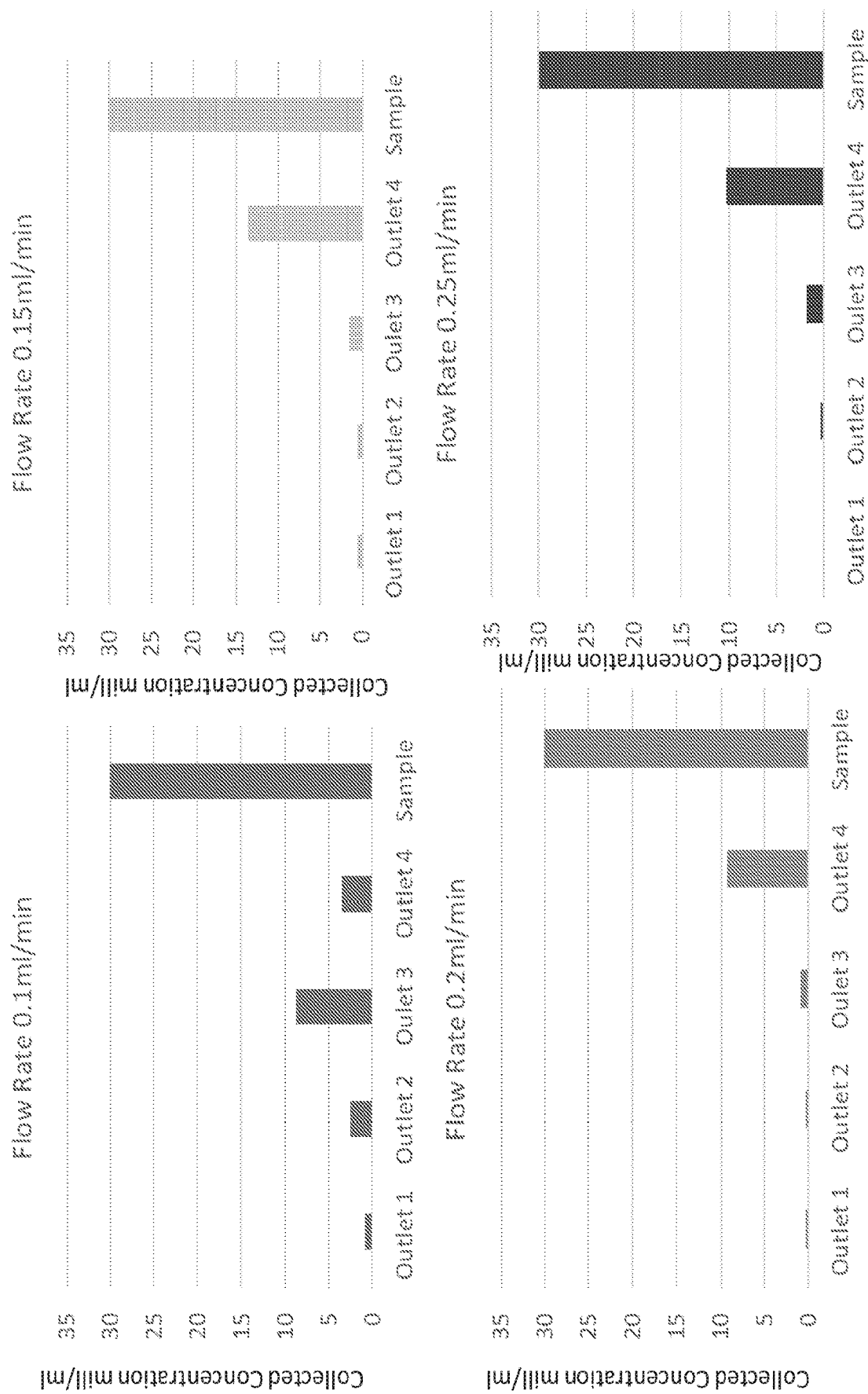
Figure 18:
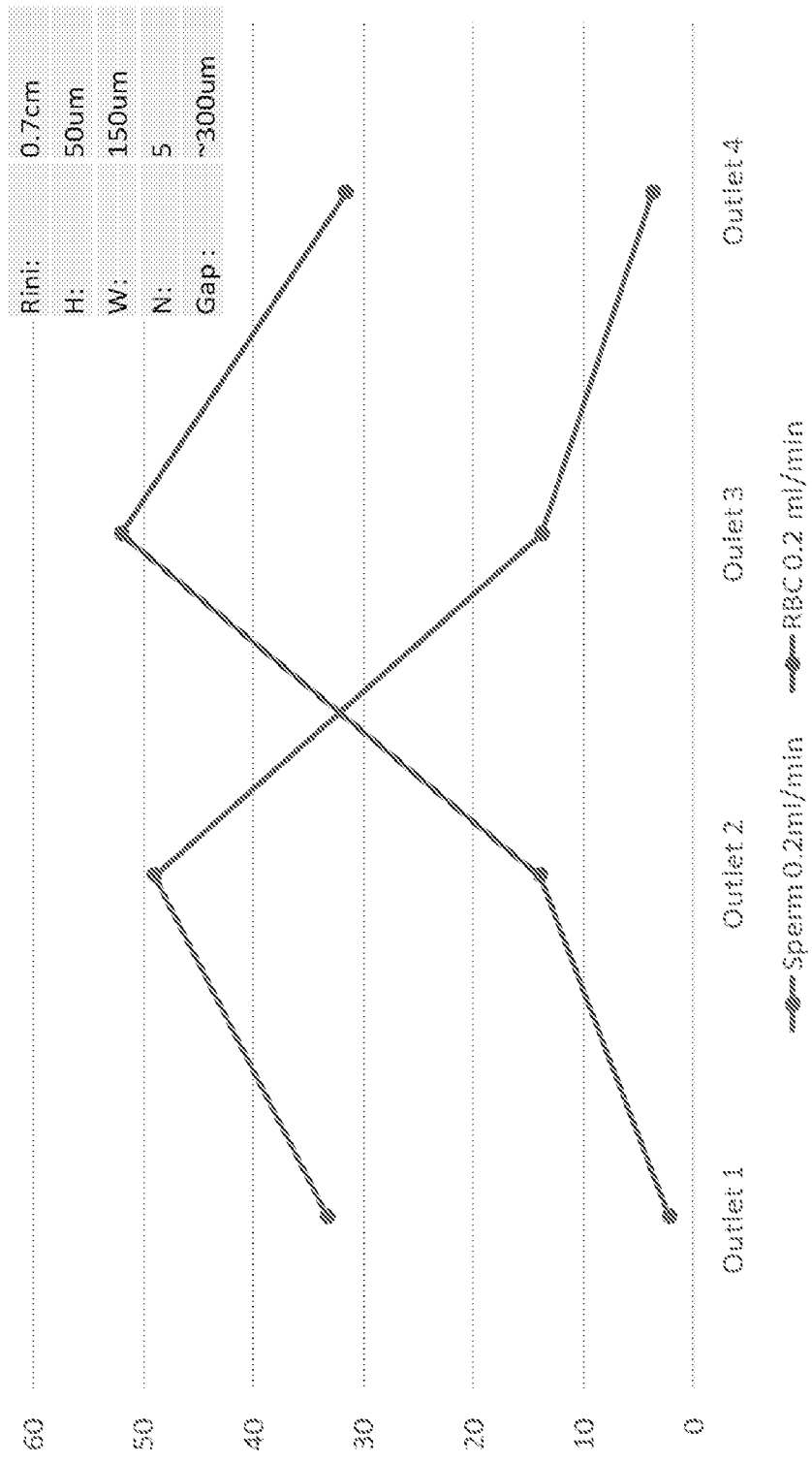
Figure 19:
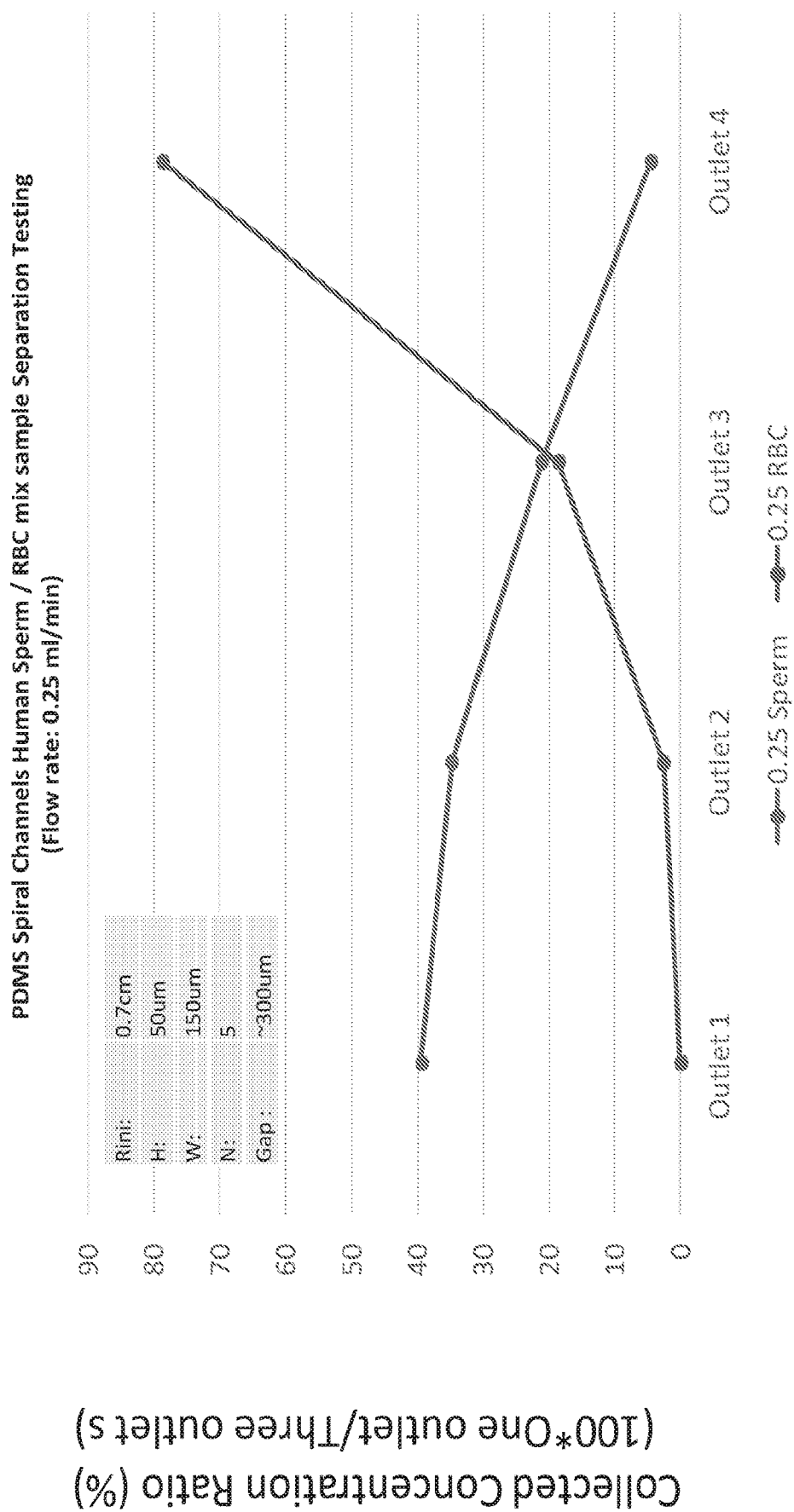
Figure 20:
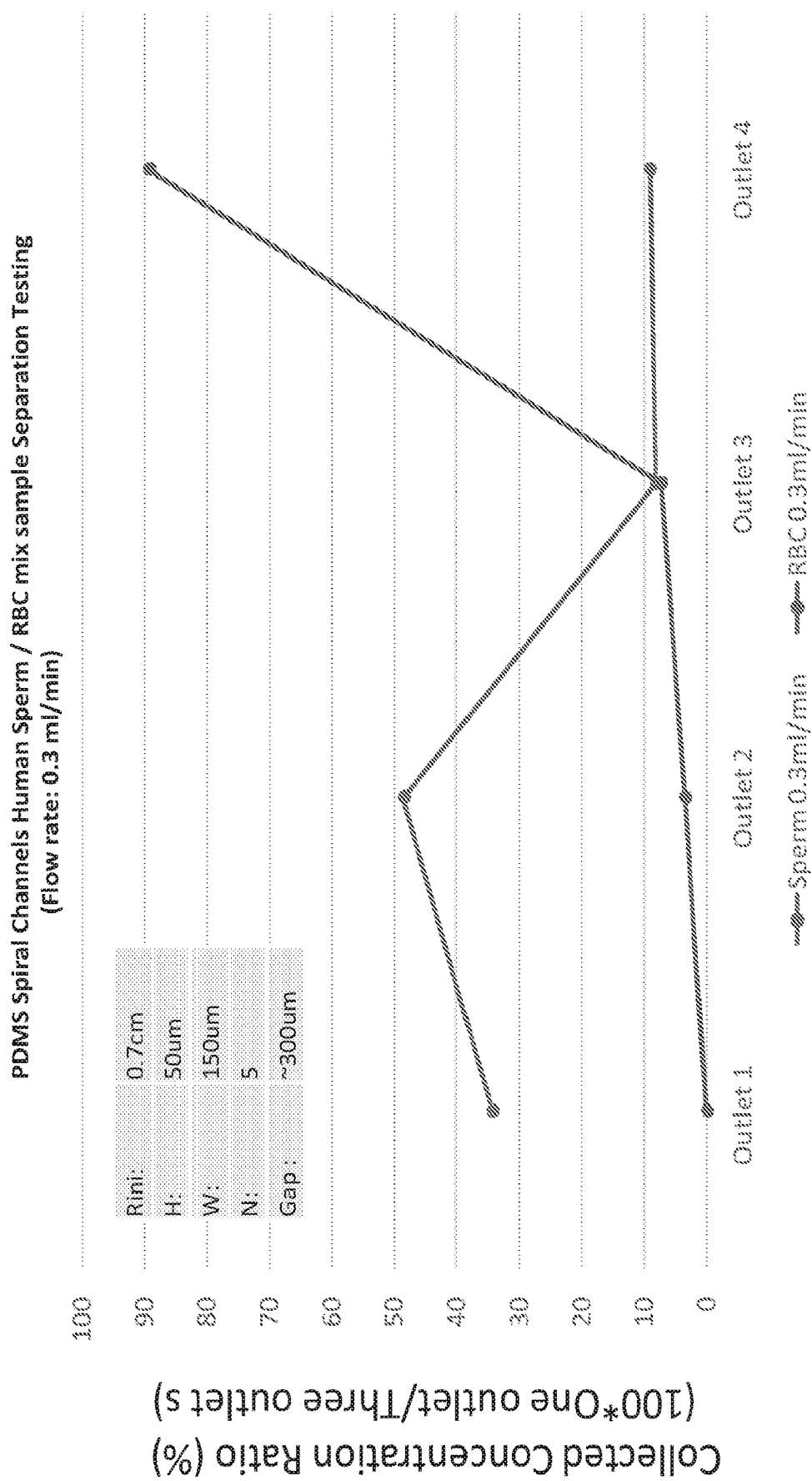
Figure 21:
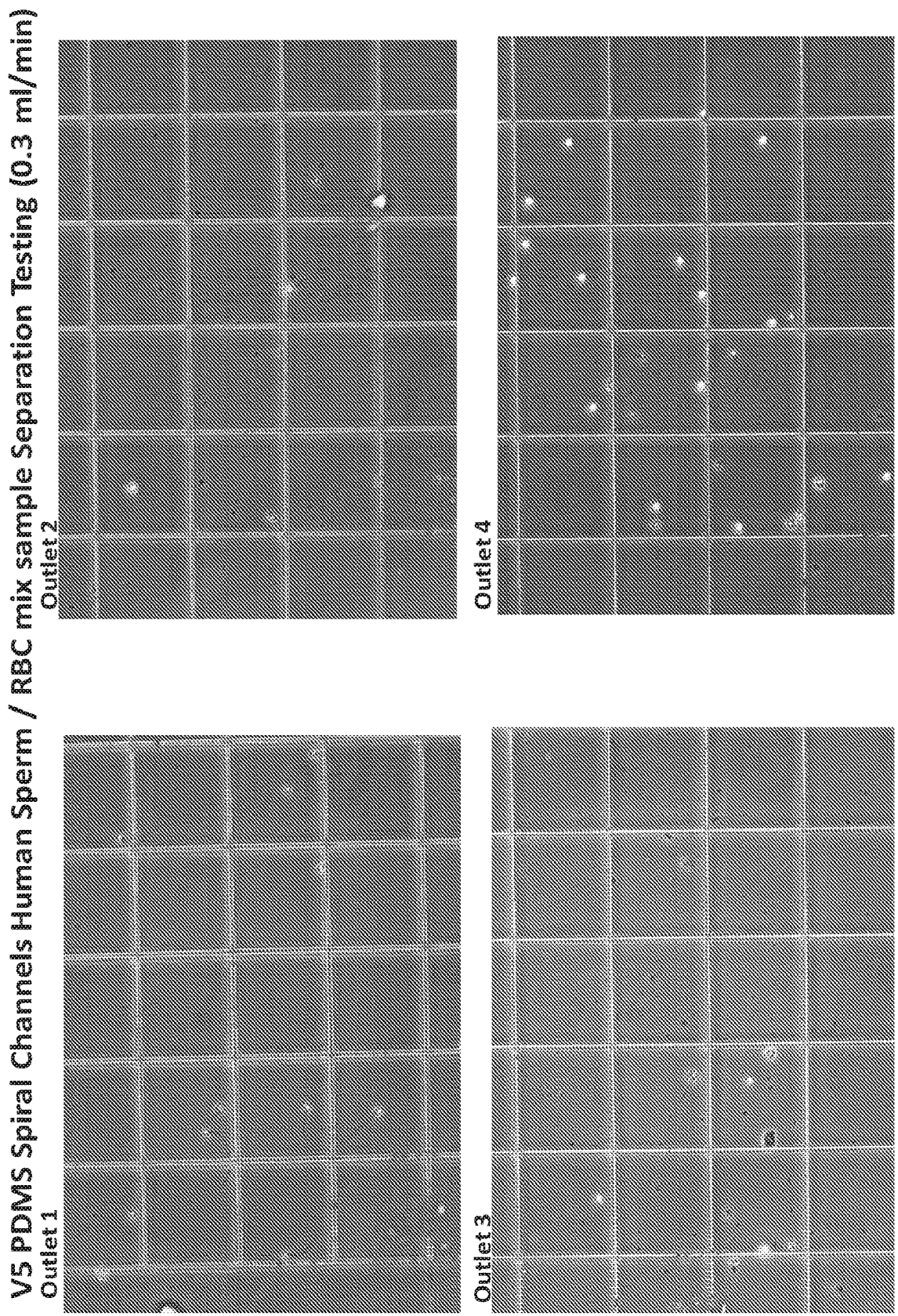
Figure 22:
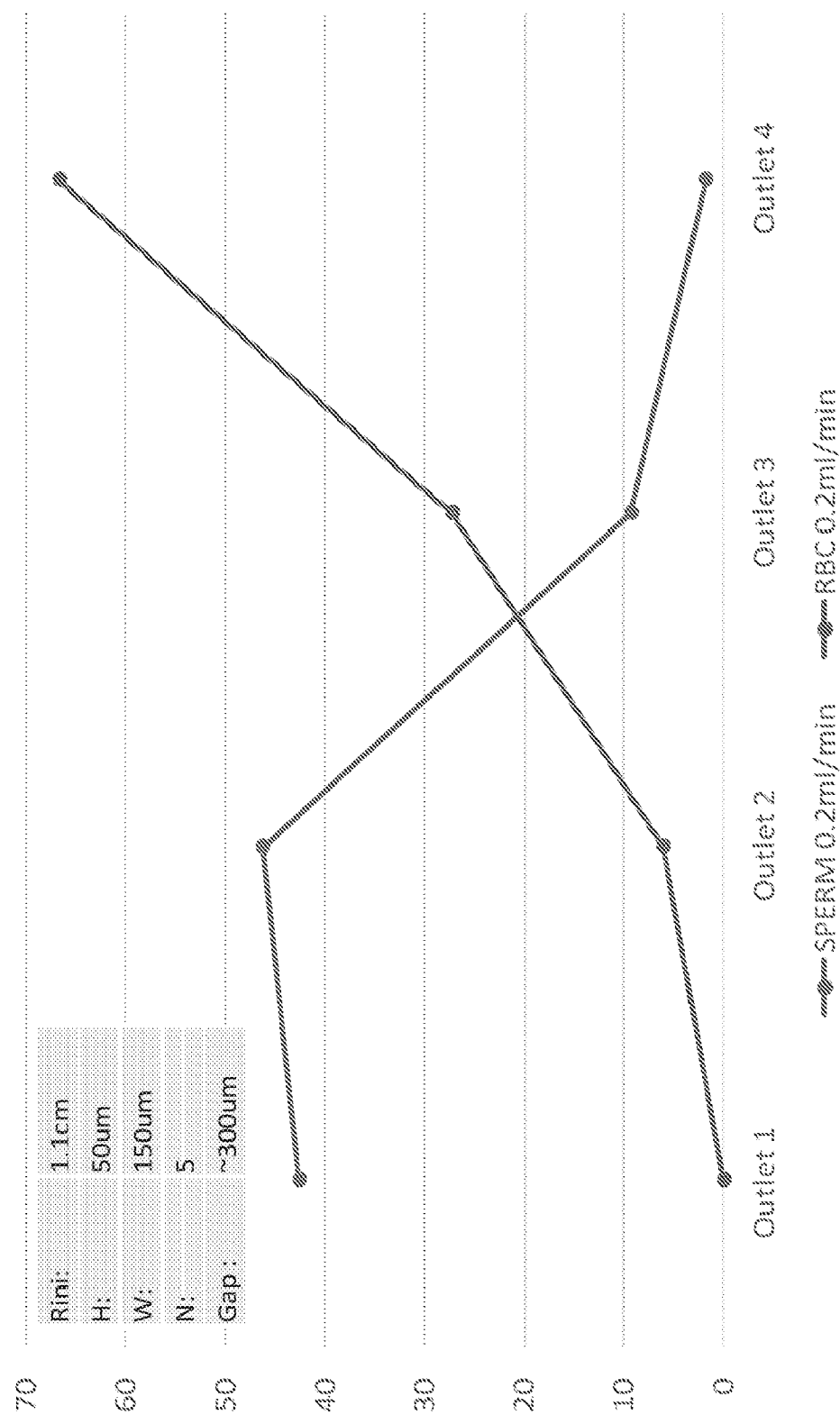

FIGS. 12A through 22 illustrate test data related to performance of a tissue sample processing system in accordance with one aspect of the invention. In particular, FIGS. 12A and 12B show that capability of sperm separation from high white blood cell (WBC) semen. FIG. 12A shows measured cell concentration on each different outlets after separation with the spiral channel. Most of the WBC are collected in the inner wall outlet (7.5 million/ml) and most of sperm are collected in the outer wall outlet (2.55 million/ml). FIG. 22B shows that 83% of sperm cells were collected in the outer wall outlet, and 94% of WBC were collected in the inner wall outlet. In addition, a small quantity of RBC are collected in the inner wall outlet as well. Thus, the spiral channel sperm separation technique also can be used for semen sample with high concentration WBC. If concentration of WBC in semen is near or higher than 1 million/ml, it is considered as Pyospermia (leukocytospermia). WBC should be removed from semen before further ART procedures. FIG. 21 shows a representative portion of a cell counting grid (e.g. MAKLER cell counting chamber) for measuring sperm population intensity among each of four outlets.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method of separating sperm cells, comprising:
   obtaining a microfluidic separating system having a fluid channel and a plurality of outlets; and
   disposing a sperm sample in the fluid channel, wherein flow of the sperm sample in the fluid channel facilitates segregation of materials in the sperm sample based on size and shape into a plurality of size and shape fractions, such that each one of the plurality of outlets receives a different size and shape fraction of the materials in the sperm sample.

2. The method of claim 1, wherein the fluid channel comprises a spiral configuration.

3. The method of claim 1, wherein the microfluidic separating system comprises:
   an inlet zone having a carrier fluid inlet to receive a carrier fluid and a tissue sample inlet to receive the tissue sample;
   an outlet zone having the plurality of outlets; and
   a transport region between the inlet zone and the outlet zone, the transport region being open to the carrier fluid and the tissue sample,
   wherein a cross-flow in the transport region facilitates segregation of the materials in the tissue sample based on size and shape.

4. The method of claim 1, wherein the material in the sperm sample associated with at least one of the plurality of outlets comprises non-motile sperm cells to form a first aliquot.

5. The method of claim 1, further comprising:
   associating a sorting system with at least one of the plurality of outlets, wherein the material in the sperm sample associated with the at least one of the plurality of outlets comprises non-motile sperm cells; and
   sorting the non-motile sperm cells into a plurality of aliquots.

6. The method of claim 5, wherein the sorting system comprises:
   an inlet to receive the material in the tissue sample associated with the at least one of the plurality of outlets;
   a plurality of aliquot storage channels; and
   a plurality of valves associated with the plurality of aliquot storage channels to facilitate separation of the plurality of aliquots into the aliquot storage channels.

7. The method of claim 4, wherein the material in the sperm sample associated with a second of the plurality of outlets comprises motile sperm cells to form a second aliquot.

8. The method of claim 4, wherein the material in the sperm sample associated with a third of the plurality of outlets comprises red blood cells.

9. The method of claim 8, further comprising introducing red blood cell antibodies into the fluid channel in order to reduce red blood cells in the first aliquot.

10. The method of claim 1, wherein the material in the sperm sample associated with a fourth of the plurality of outlets comprises at least one of spermatogonial stem cells and sperm precursor cells.

11. The method of claim 1, wherein the plurality of outlets includes isolated material of at least one of aneuploid sperm cells and euploid sperm cells.

12. The method of claim 1, wherein the method is performed without addition of reagents.

13. The method of claim 1, further comprising cryopreserving at least one aliquot from the plurality of outlets to freeze the material in the aliquot.

14. The method of claim 3, wherein the cross-flow in the fluid channel facilitates segregation of non-motile sperm cells within the inner fluid flow layer and one of the plurality of outlets comprises non-motile sperm.

15. The method of claim 14, further comprising sorting the non-motile sperm cells into a plurality of aliquots, wherein each of the plurality of aliquots comprises from about 1 to about 20 non-motile sperm cells.

16. The system of claim 15, wherein each of the plurality of aliquots comprises a single non-motile sperm cell.

17. The system of claim 2, wherein the spiral configuration includes an inner flow layer and an outer flow layer and non-motile sperm are collected in the inner flow layer and removed via one of the plurality of outlets.

* * * * *